US00RE47884E

(19) United States
(12) Reissued Patent
Duignan et al.

(10) Patent Number: US RE47,884 E
(45) Date of Reissued Patent: Mar. 3, 2020

(54) DISPENSER

(71) Applicant: EURO-CELTIQUE S.A., Luxembourg (LU)

(72) Inventors: Cathal Duignan, Carrick on Shannon (IE); Iain Grierson McDerment, Melbourn (GB)

(73) Assignee: EURO-CELTIQUE S.A., Luxembourg (LU)

(21) Appl. No.: 15/727,225

(22) Filed: Oct. 6, 2017

Related U.S. Patent Documents

Reissue of:
(64) Patent No.: 9,572,945
Issued: Feb. 21, 2017
Appl. No.: 14/355,779
PCT Filed: Oct. 31, 2012
PCT No.: PCT/GB2012/052709
§ 371 (c)(1),
(2) Date: May 1, 2014
PCT Pub. No.: WO2013/064821
PCT Pub. Date: May 10, 2013

(30) Foreign Application Priority Data

Nov. 1, 2011 (GB) ..... 1118845.5

(51) Int. Cl.

| | |
|---|---|
| ***A61M 15/00*** | (2006.01) |
| ***A61M 11/04*** | (2006.01) |
| ***A61M 16/12*** | (2006.01) |
| ***G06M 1/08*** | (2006.01) |
| ***G06M 1/04*** | (2006.01) |

(52) U.S. Cl.
CPC ..... *A61M 15/0073* (2014.02); *A61M 11/04* (2013.01); *A61M 15/009* (2013.01); *A61M 15/0021* (2014.02); *A61M 15/0026* (2014.02); *A61M 15/0075* (2014.02); *A61M 15/0091* (2013.01); *A61M 15/0093* (2014.02); *A61M 16/12* (2013.01); *G06M 1/04* (2013.01); *G06M 1/083* (2013.01)

(58) Field of Classification Search
CPC ..... A61M 15/0073; A61M 15/0093; A61M 15/0021; A61M 11/04; A61M 16/12; A61M 15/0026; A61M 15/0075
See application file for complete search history.

(56) References Cited

U.S. PATENT DOCUMENTS

| | | | |
|---|---|---|---|
| 5,119,806 | A | 6/1992 | Palson et al. |
| 6,422,234 | B1 | 7/2002 | Bacon |
| 6,446,627 | B1 | 9/2002 | Bowman et al. |

(Continued)

FOREIGN PATENT DOCUMENTS

| | | | |
|---|---|---|---|
| CN | 1798589 | A | 7/2006 |
| CN | 101232913 | A | 7/2008 |

(Continued)

OTHER PUBLICATIONS

Eurasian Patent Office Search Report dated Dec. 1, 2016 issued in Appln No. 201691179.

(Continued)

*Primary Examiner* — Jeffrey L Gellner
(74) *Attorney, Agent, or Firm* — Nixon & Vanderhye P.C.

(57) ABSTRACT

Dispensers, in particular dispensers for dispensing a dose of a gaseous, gas borne or droplet substance from a substance source and dispensers containing dosage counters are described herein.

21 Claims, 23 Drawing Sheets

(56) References Cited

U.S. PATENT DOCUMENTS

| | | | | |
|---|---|---|---|---|
| 6,866,037 | B1 | 3/2005 | Aslin et al. | |
| 6,866,038 | B2 | 3/2005 | Bacon | |
| 7,036,505 | B2 | 5/2006 | Bacon et al. | |
| 7,047,964 | B2 | 5/2006 | Bacon | |
| 7,225,805 | B2 | 6/2007 | Bacon | |
| 7,575,003 | B2 | 8/2009 | Rasmussen et al. | |
| 7,678,073 | B2 | 3/2010 | Griffiths | |
| 7,721,731 | B2 | 5/2010 | Bacon | |
| 7,814,900 | B2 | 10/2010 | Bacon | |
| 7,976,234 | B2 | 7/2011 | May | |
| 7,988,016 | B2 | 8/2011 | Klein | |
| 8,167,840 | B2 | 5/2012 | Matusch | |
| 8,287,493 | B2 | 10/2012 | Matusch | |
| 8,308,028 | B2 | 11/2012 | Bacon | |
| 8,329,271 | B2 | 12/2012 | Bacon | |
| 8,408,208 | B2 | 4/2013 | Bacon | |
| 8,992,487 | B2 | 3/2015 | Eich et al. | |
| 2004/0025870 | A1* | 2/2004 | Harrison | A61M 15/0091 128/202.17 |
| 2006/0096594 | A1* | 5/2006 | Bonney | A61M 15/0065 128/202.17 |
| 2006/0175345 | A1* | 8/2006 | Lu | A61M 15/009 222/23 |
| 2006/0243275 | A1* | 11/2006 | Ruckdeschel | A61M 15/0091 128/200.23 |
| 2007/0062522 | A1* | 3/2007 | Bacon | A61M 15/0095 128/200.23 |
| 2007/0246042 | A1 | 10/2007 | Purkins et al. | |
| 2008/0013557 | A1 | 1/2008 | Siemens et al. | |
| 2008/0077083 | A1 | 3/2008 | Griffiths | |
| 2008/0135575 | A1* | 6/2008 | Ingram | A61M 15/009 222/36 |
| 2008/0135576 | A1 | 6/2008 | Bacon | |
| 2008/0168984 | A1* | 7/2008 | Lintern | A61M 15/009 128/200.23 |
| 2009/0211578 | A1 | 8/2009 | Fletcher | |
| 2009/0229604 | A1 | 9/2009 | Pearson et al. | |
| 2010/0012115 | A1 | 1/2010 | Bacon | |
| 2010/0036326 | A1 | 2/2010 | Matusch | |
| 2011/0054412 | A1 | 3/2011 | Eich | |
| 2011/0259324 | A1 | 10/2011 | Hochrainer | |
| 2012/0017900 | A1 | 1/2012 | Bacon | |
| 2012/0111323 | A1 | 5/2012 | Bacon et al. | |
| 2012/0197186 | A1 | 8/2012 | Matusch | |
| 2016/0038696 | A1* | 2/2016 | Duignan | A61M 15/0026 128/200.23 |

FOREIGN PATENT DOCUMENTS

| | | | |
|---|---|---|---|
| GB | 2 372 542 A | 8/2002 | |
| GB | 2372542 | 8/2002 | |
| GB | 2461752 | 1/2010 | |
| JP | 2006-518238 | 9/2004 | |
| JP | 2006-518238 A | 8/2006 | |
| JP | 2008-532678 | 9/2006 | |
| JP | 2008-532678 A | 8/2008 | |
| RU | 2 162 346 C2 | 1/1997 | |
| TW | 200824741 | 6/2008 | |
| TW | 200902112 | 1/2009 | |
| TW | 200942284 | 10/2009 | |
| WO | WO 97/00703 A1 | 1/1997 | |
| WO | WO2004/073776 | 9/2004 | |
| WO | WO 2004/073776 A1 | 9/2004 | |
| WO | 2005/060535 | 7/2005 | |
| WO | WO2006/097756 | 9/2006 | |
| WO | 2010/103315 | 9/2010 | |
| WO | WO 2010103315 A2 * | 9/2010 | A61M 15/0065 |

OTHER PUBLICATIONS

International Search Report for PCT/GB2012/052709 dated Jan. 21, 2013.

Written Opinion of the International Searching Authority dated Jan. 21, 2013.

International Preliminary Report on Patentability dated May 6, 2014 with Written Opinion, issued in corresponding International Application No. PCT/GB2012/052709.

* cited by examiner

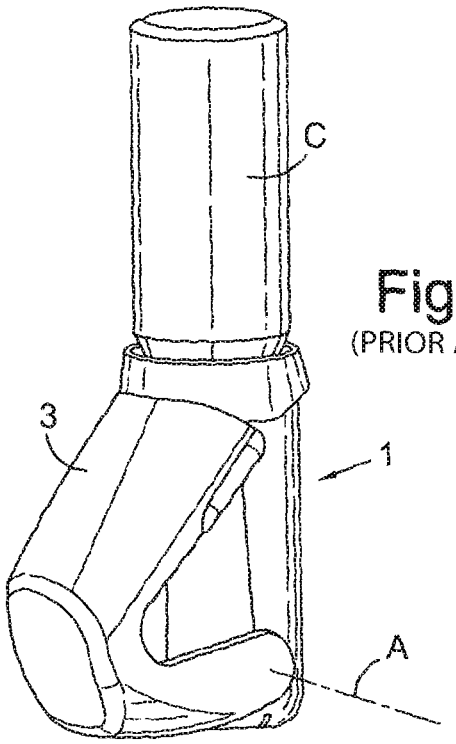
Fig.1 Amended
(PRIOR ART)
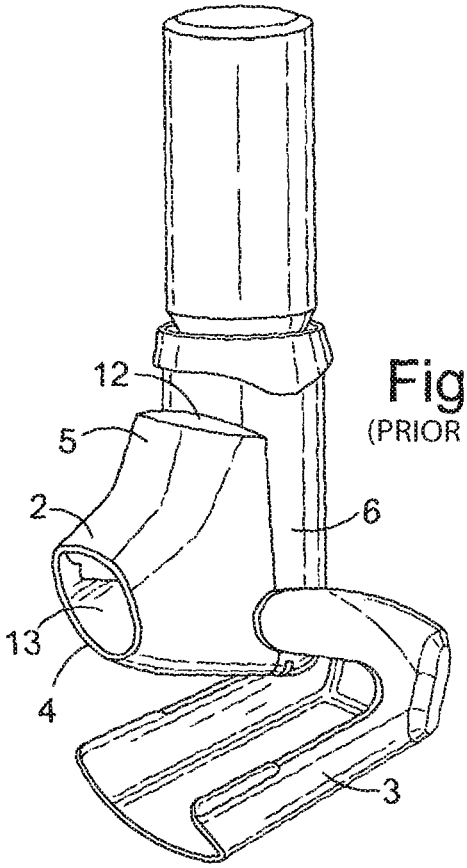
Fig.2 Amended
(PRIOR ART)
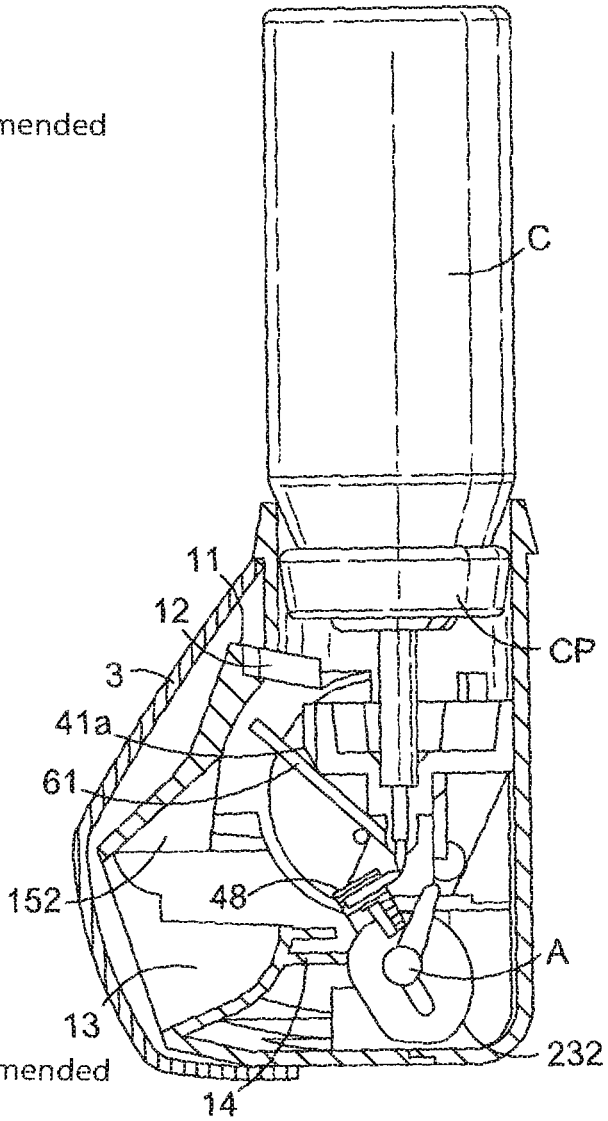
Fig.3 Amended
(PRIOR ART)

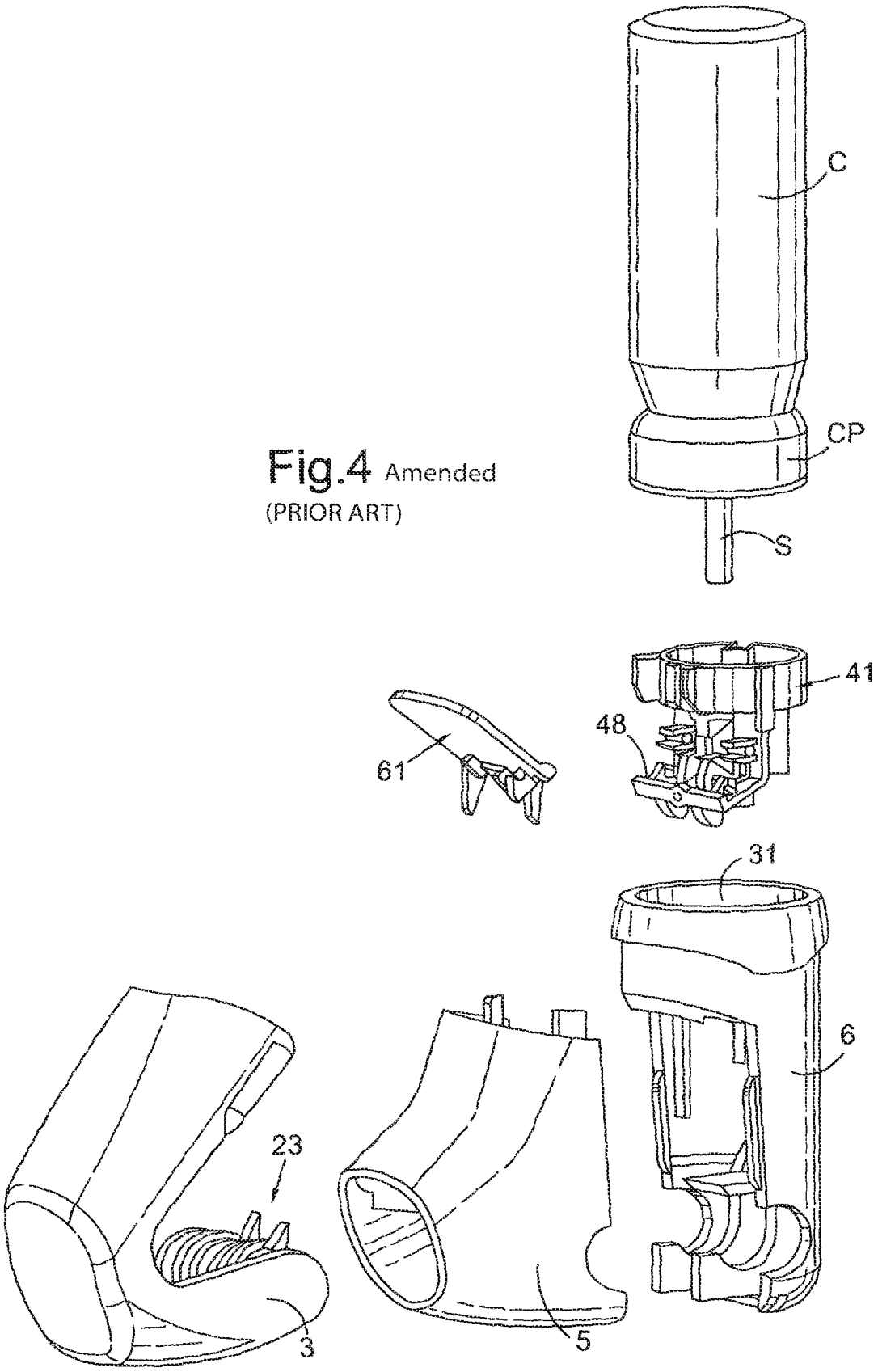
Fig.4 Amended
(PRIOR ART)

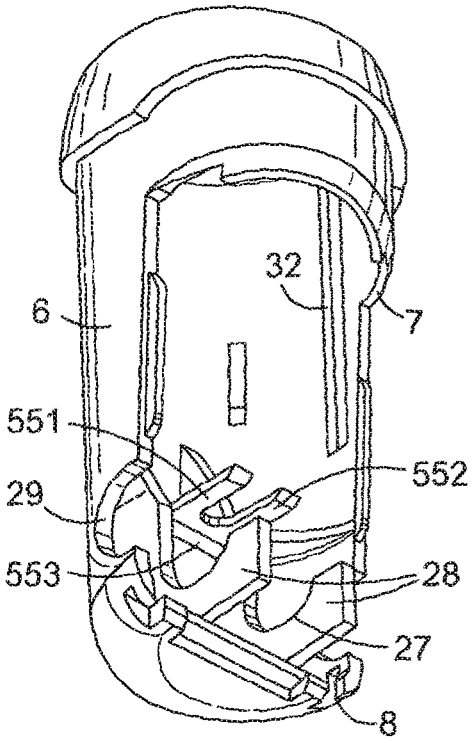
Fig.5a Amended
(PRIOR ART)

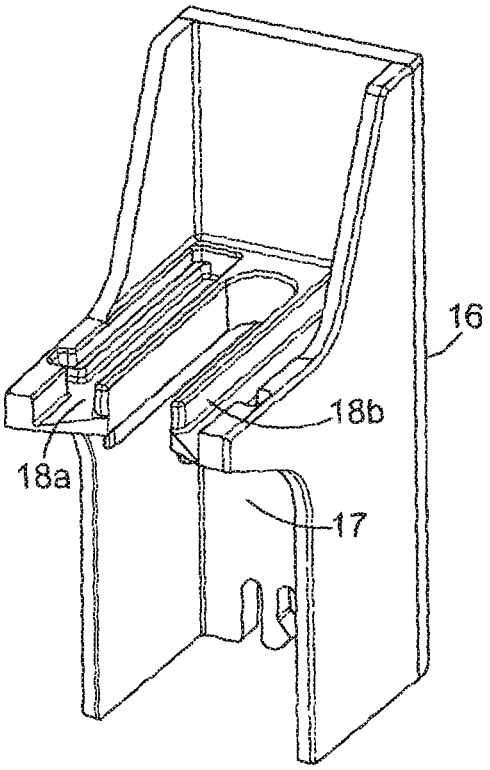
Fig.5e
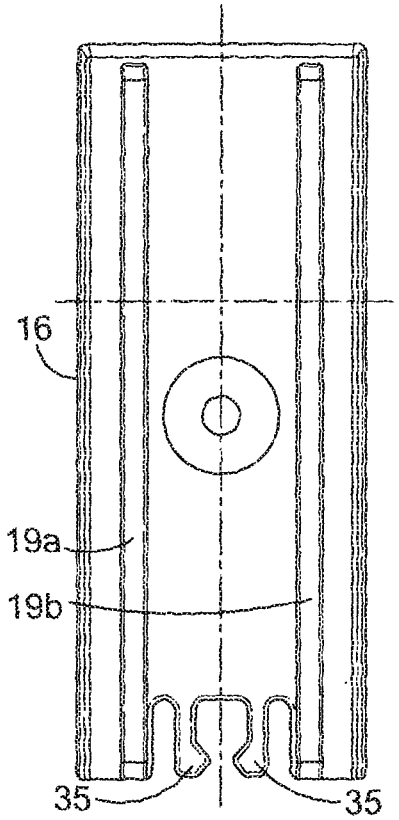
Fig.5f
Amended Fig.6
(PRIOR ART)
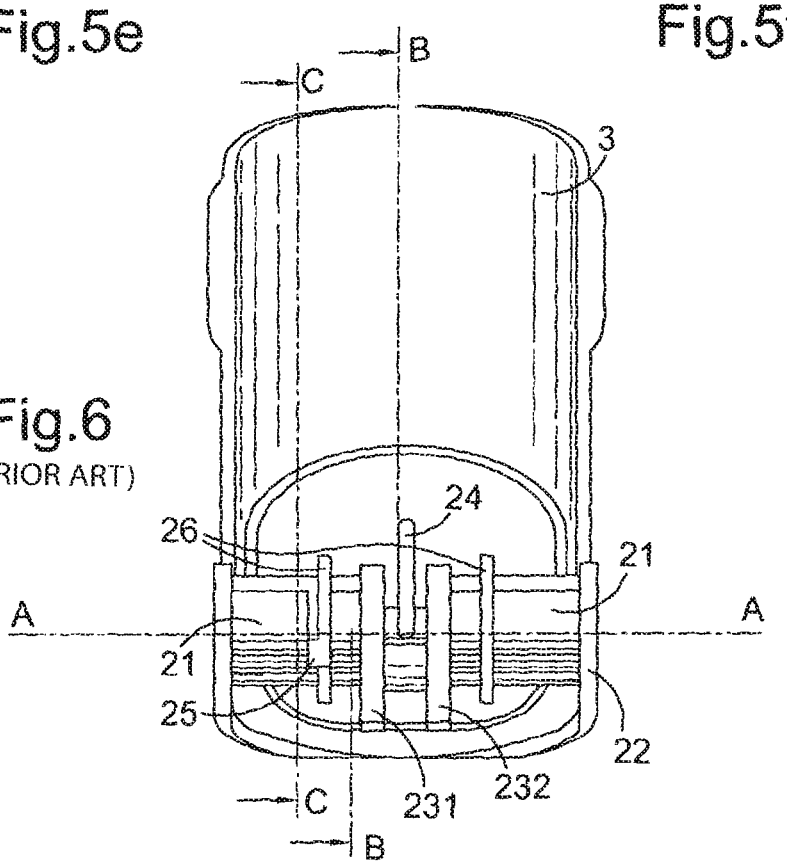

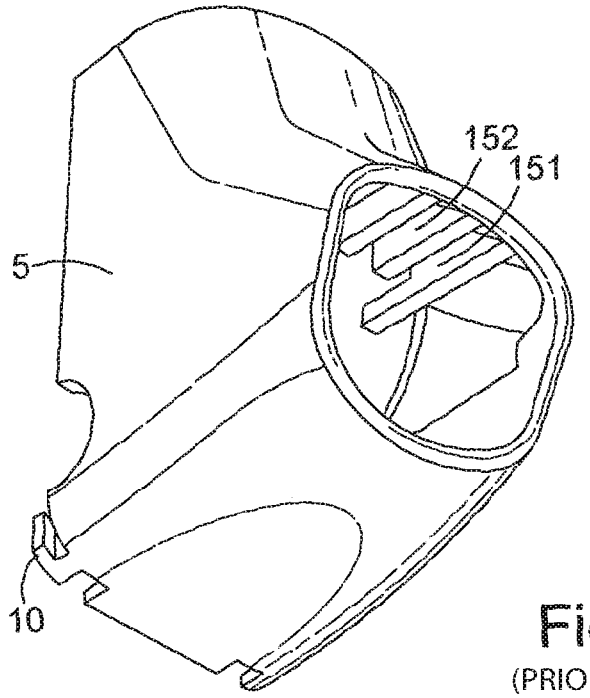
Fig.7 Amended
(PRIOR ART)
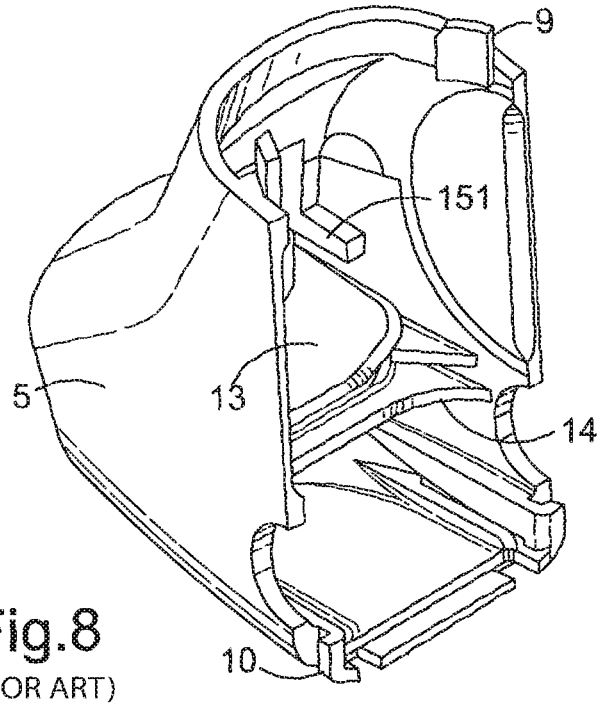
Amended Fig.8
(PRIOR ART)

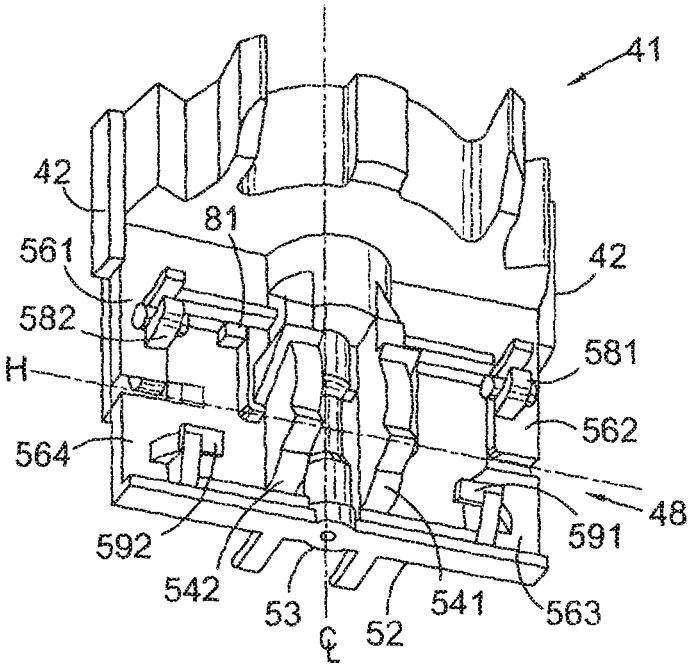
Amended Fig.9
(PRIOR ART)
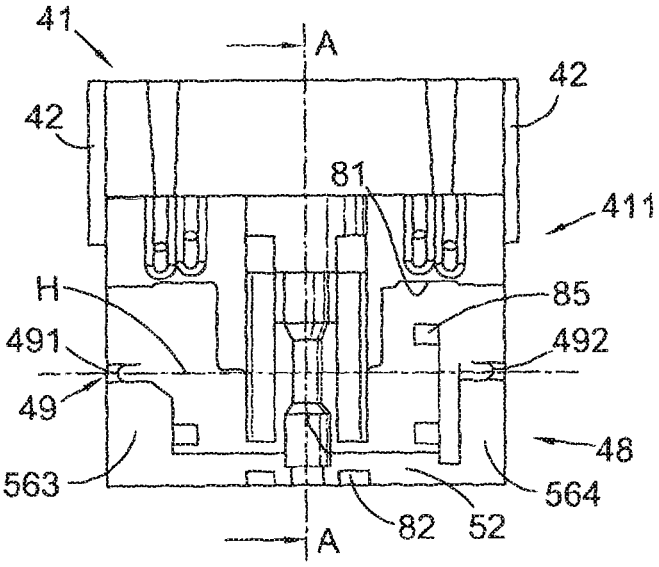
Fig.10 Amended
(PRIOR ART)
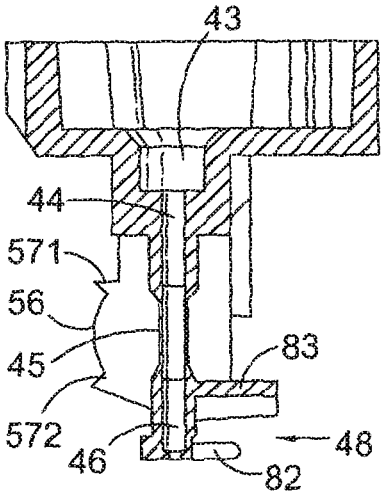
Amended Fig.11
(PRIOR ART)

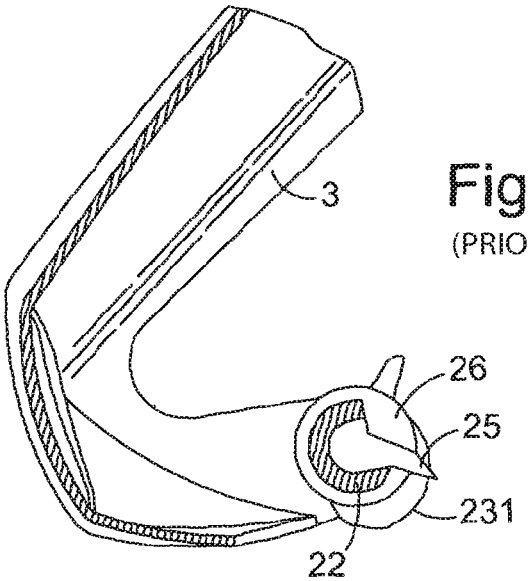
Fig.12 Amended
(PRIOR ART)
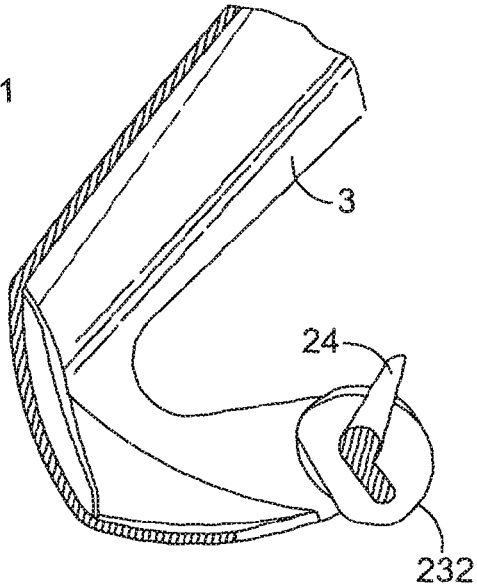
Amended Fig.13
(PRIOR ART)
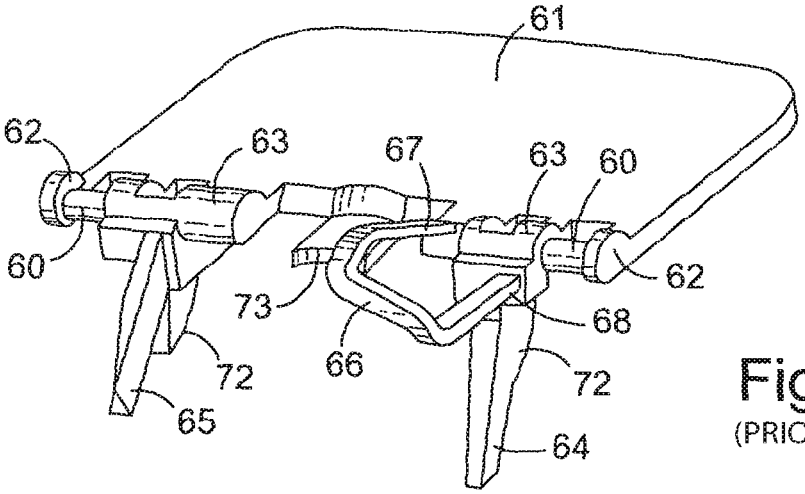
Fig.14 Amended
(PRIOR ART)

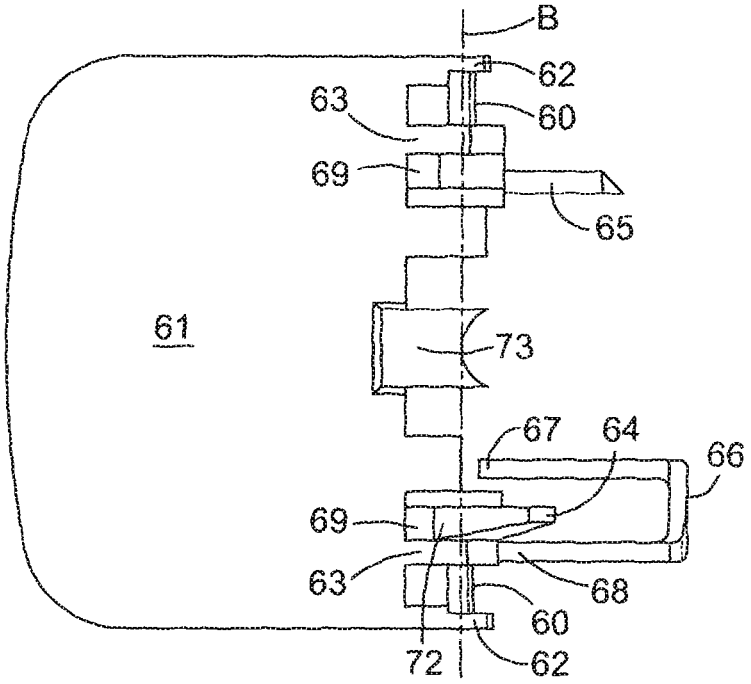
Fig.15 Amended
(PRIOR ART)
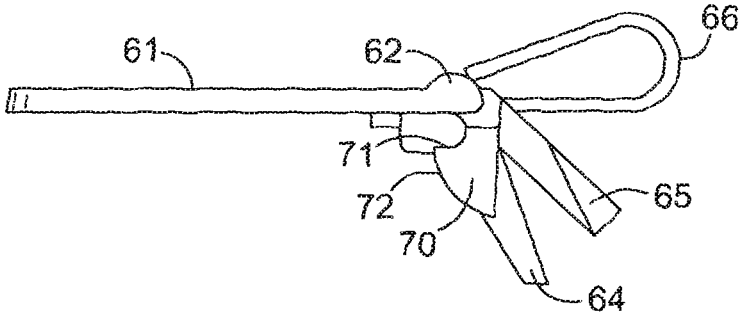
Fig.16 Amended
(PRIOR ART)

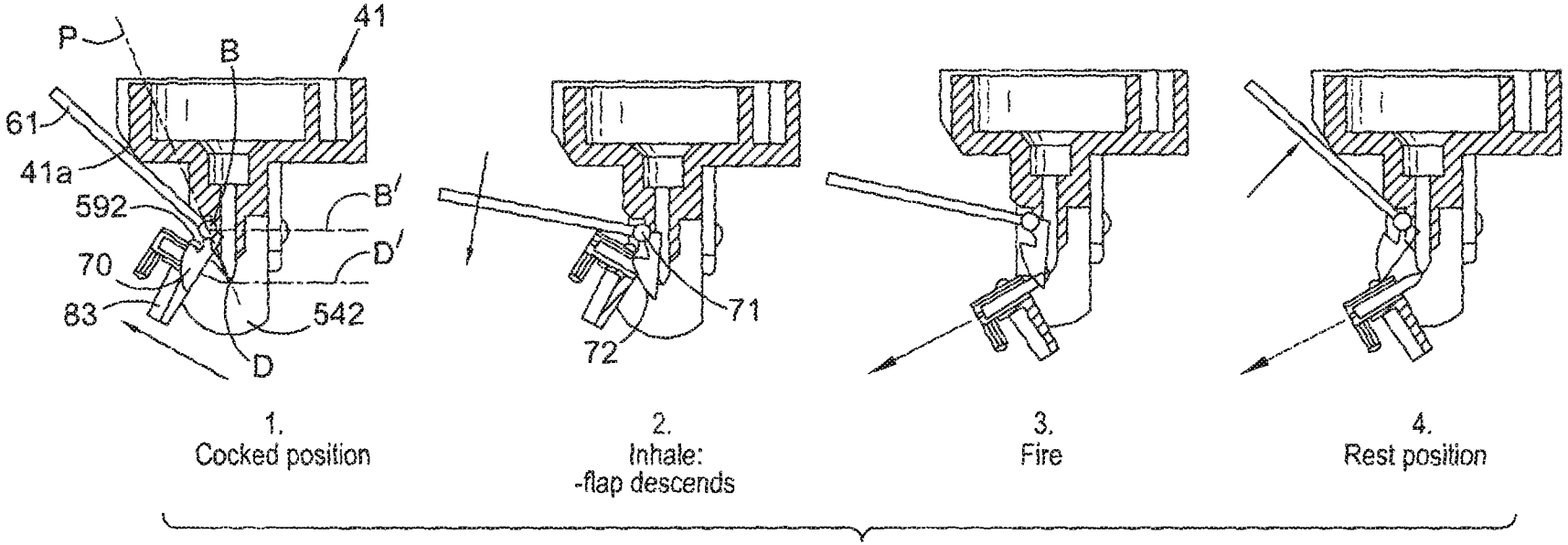
Fig.17 Amended
(PRIOR ART)

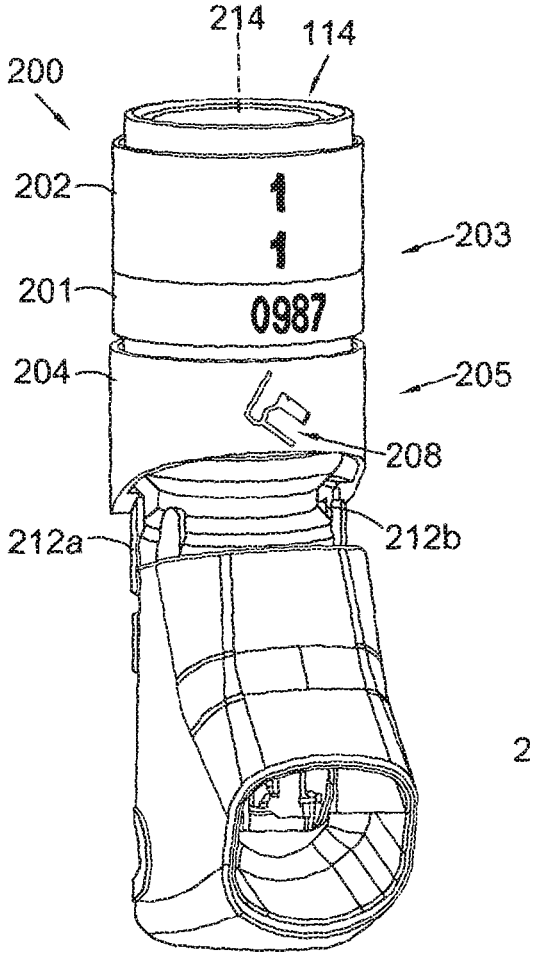
Fig.18a Amended
(PRIOR ART)
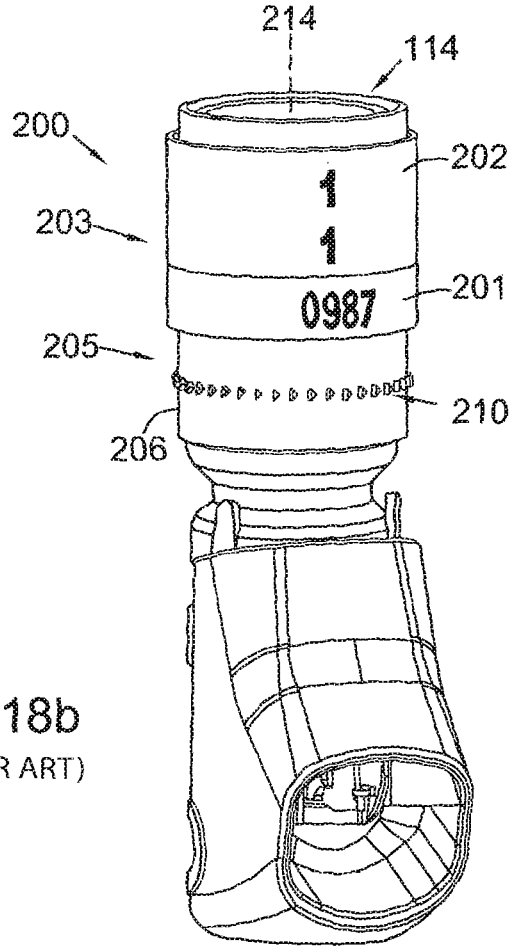
Amended Fig.18b
(PRIOR ART)

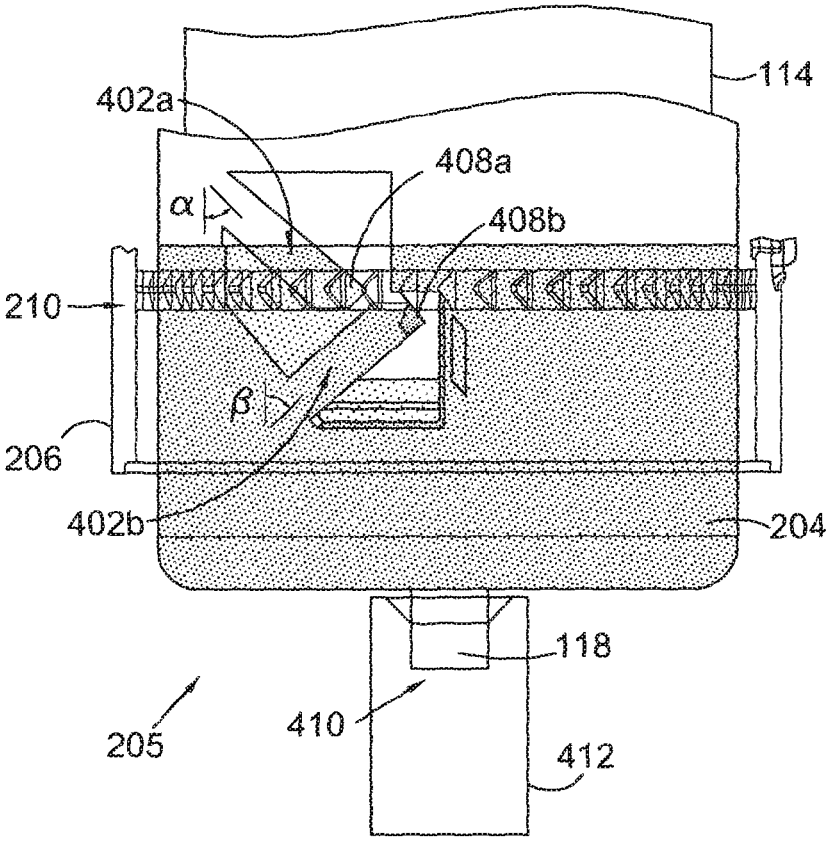
Fig.19a Amended
(PRIOR ART)
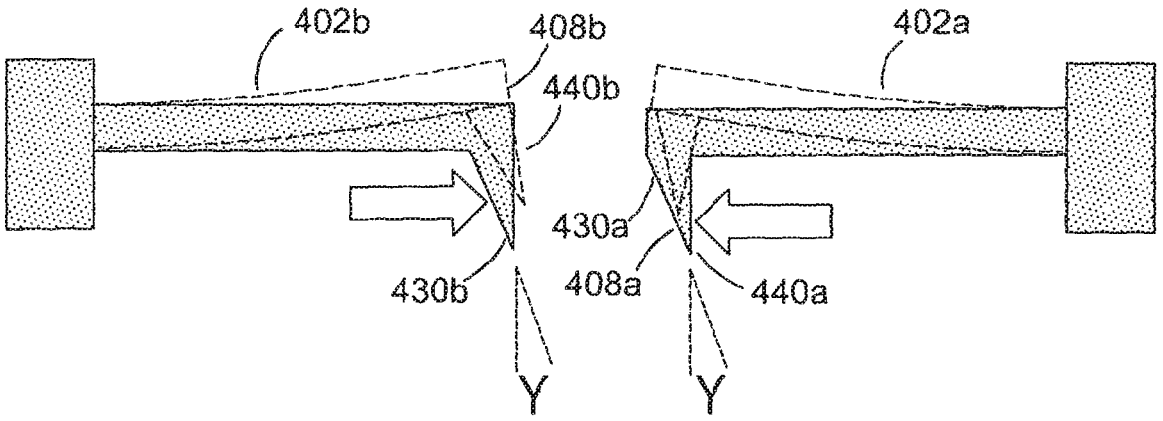
Fig.19b Amended
(PRIOR ART)

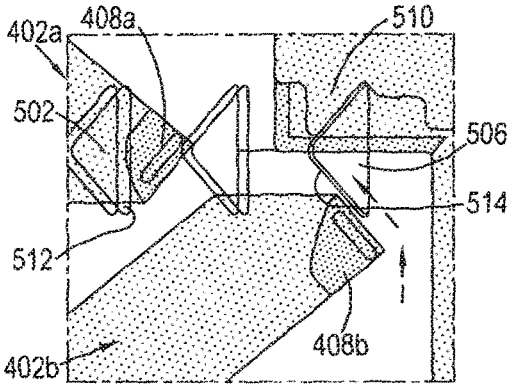
Fig.20A Amended
(PRIOR ART)
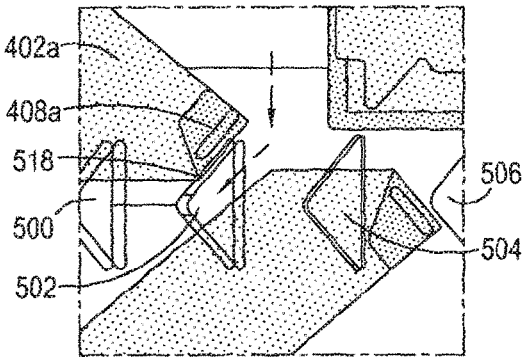
Fig.21A Amended
(PRIOR ART)
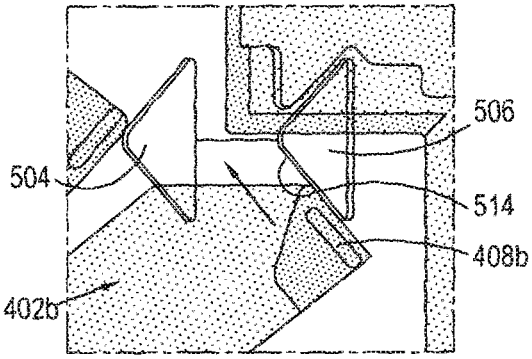
Fig.20B Amended
(PRIOR ART)
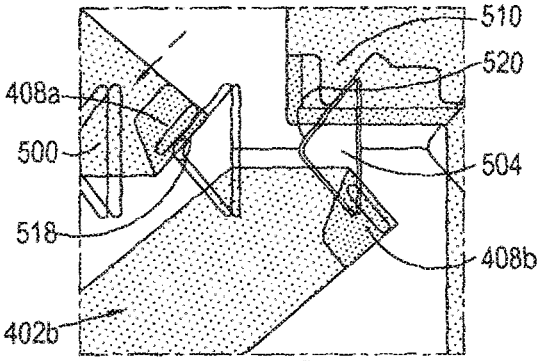
Fig.21B Amended
(PRIOR ART)
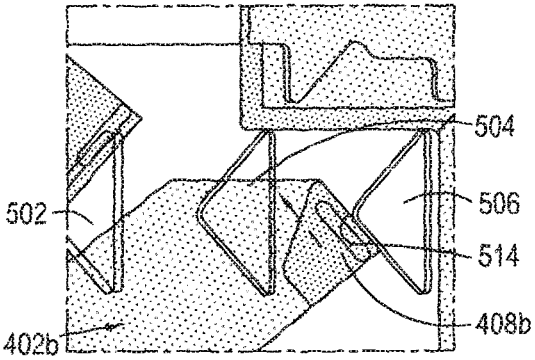
Fig.20C Amended
(PRIOR ART)
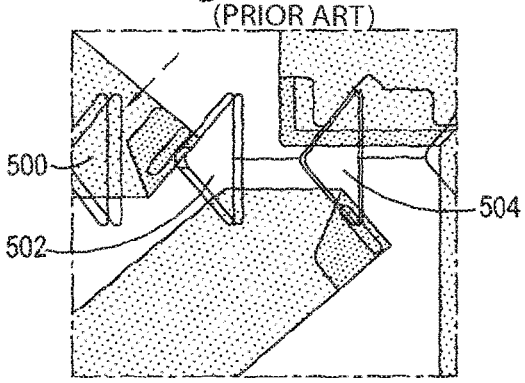
Fig.21C Amended
(PRIOR ART)
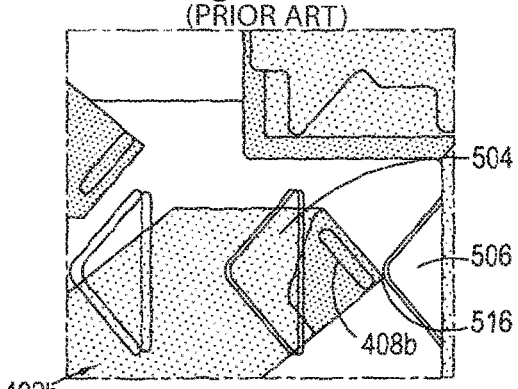
Fig.20D Amended
(PRIOR ART)
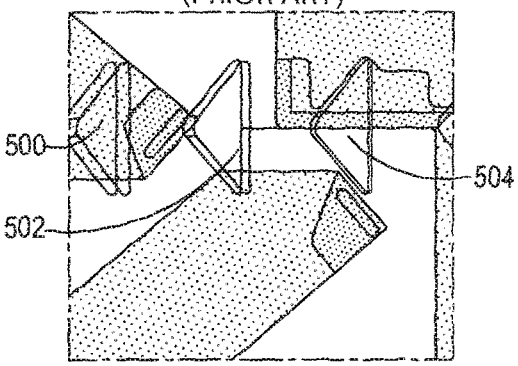
Fig.21D Amended
(PRIOR ART)

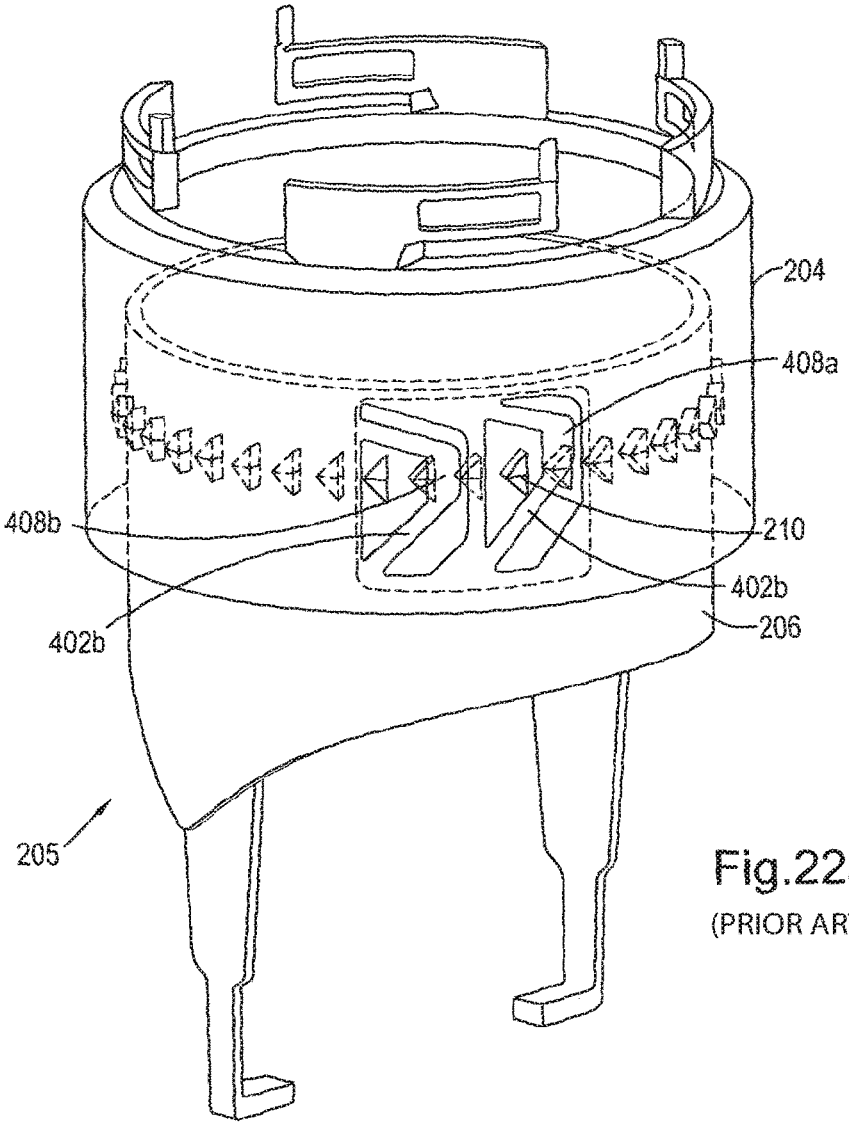
Fig.22a Amended
(PRIOR ART)
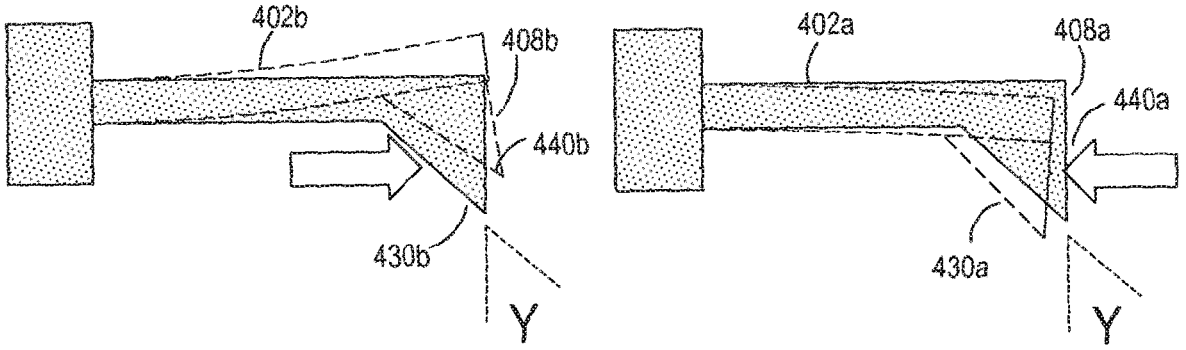
Fig.22b Amended
(PRIOR ART)

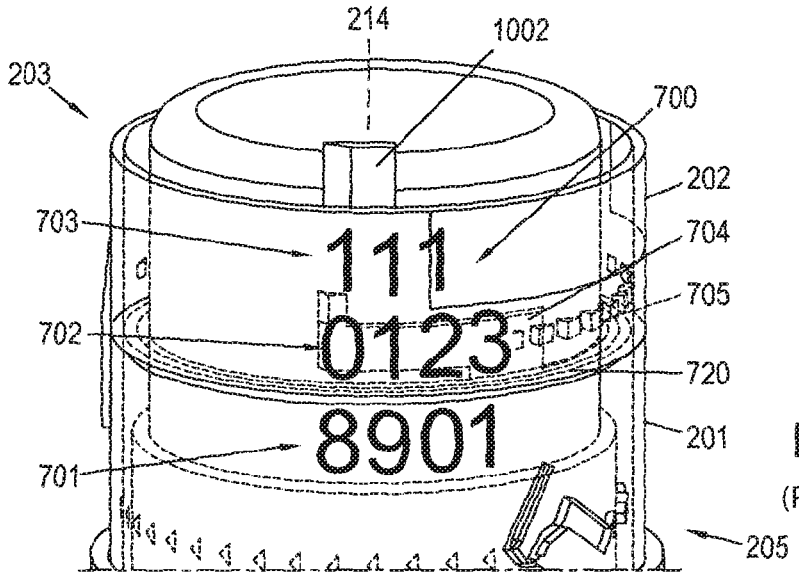
Fig.25 Amended
(PRIOR ART)
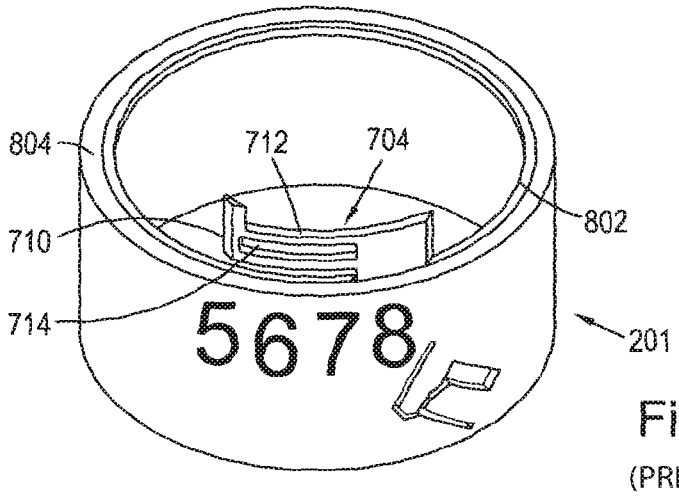
Fig.26 Amended
(PRIOR ART)
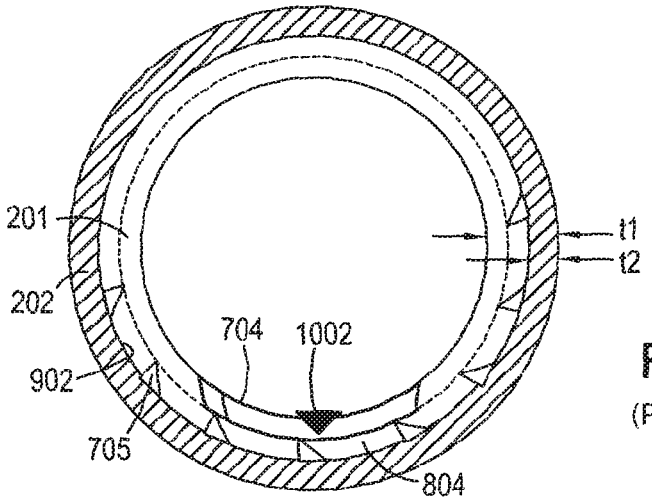
Fig.27 Amended
(PRIOR ART)

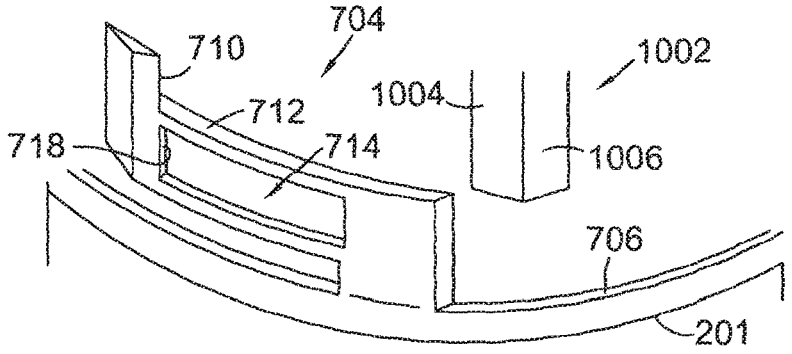
Fig.28a Amended
(PRIOR ART)
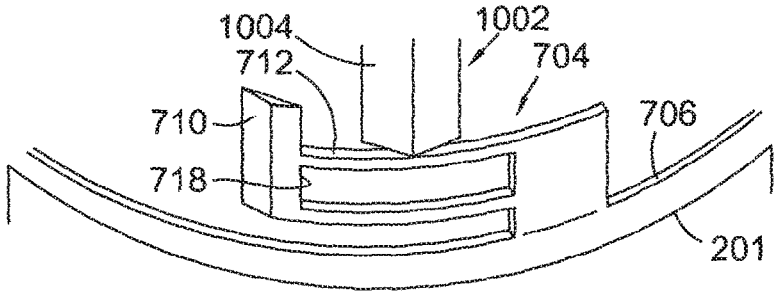
Fig.28b Amended
(PRIOR ART)
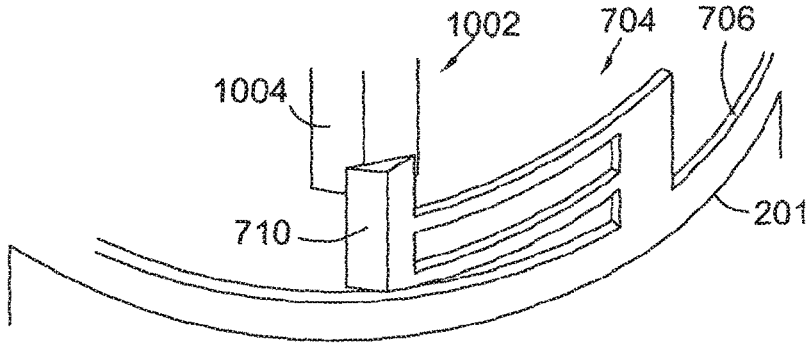
Fig.28c Amended
(PRIOR ART)
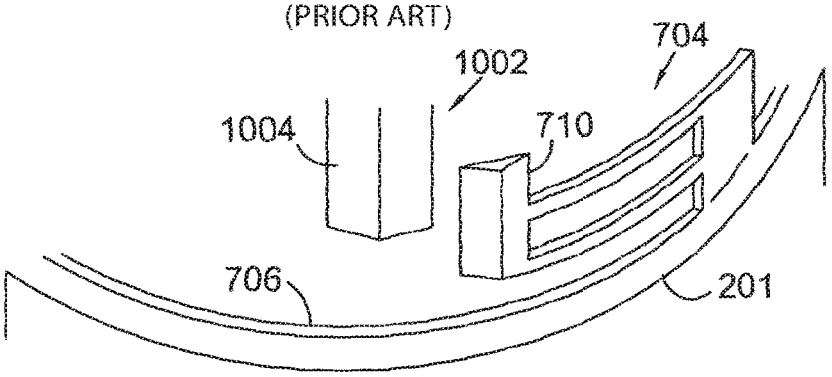
Fig.28d Amended
(PRIOR ART)

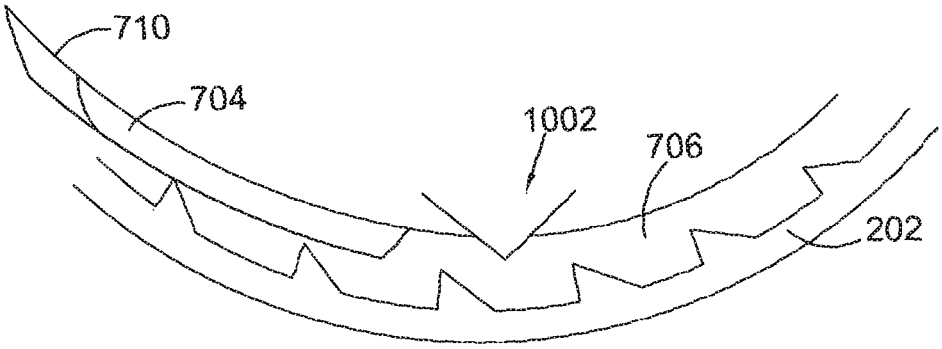
Fig.29a Amended
(PRIOR ART)
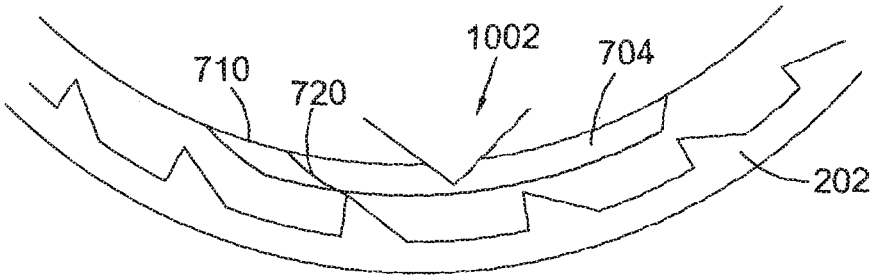
Fig.29b Amended
(PRIOR ART)
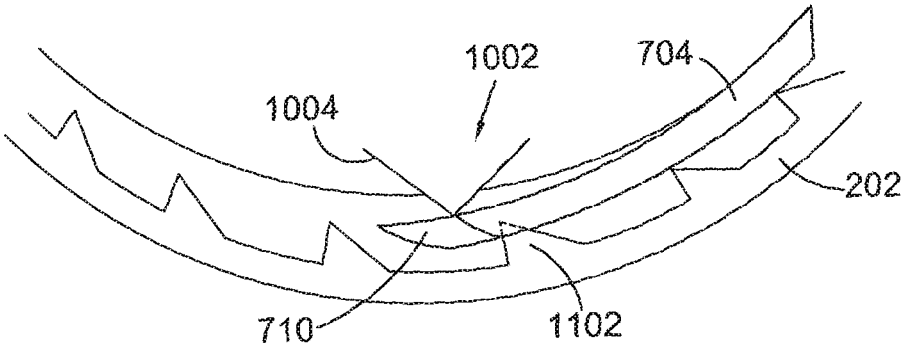
Fig.29c Amended
(PRIOR ART)
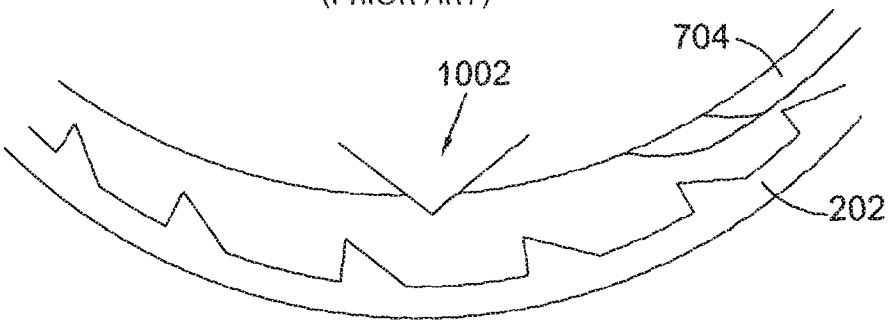
Fig.29d Amended
(PRIOR ART)

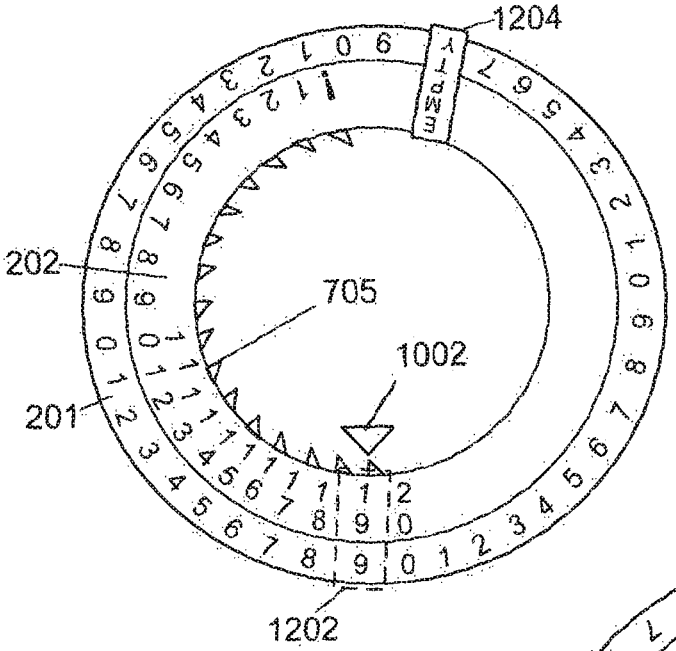
Fig.30a
Amended
(PRIOR ART)
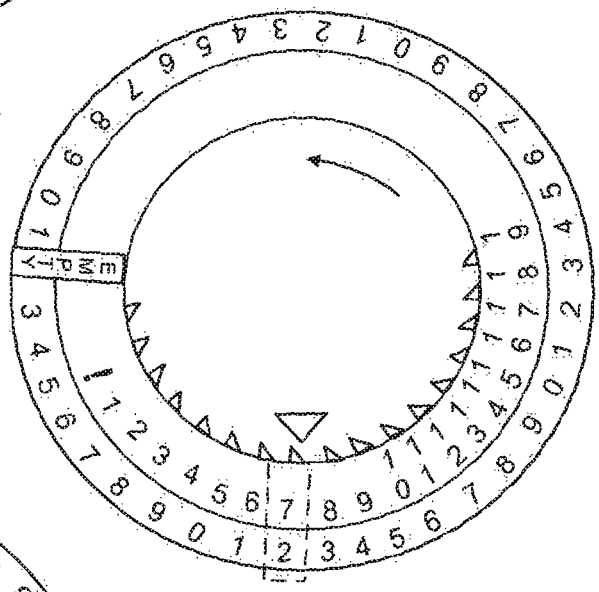
Fig.30b
Amended
(PRIOR ART)
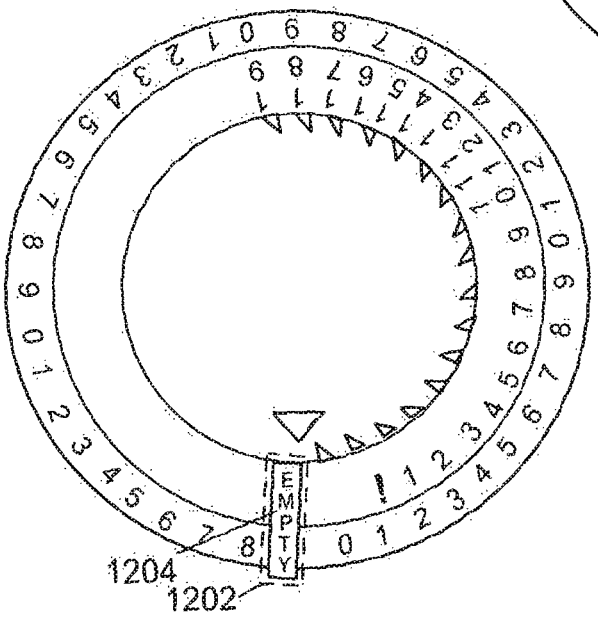
Fig.30c
Amended
(PRIOR ART)

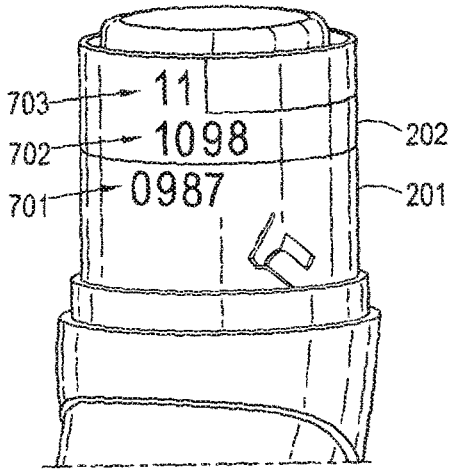
Fig.31 Amended
(PRIOR ART)
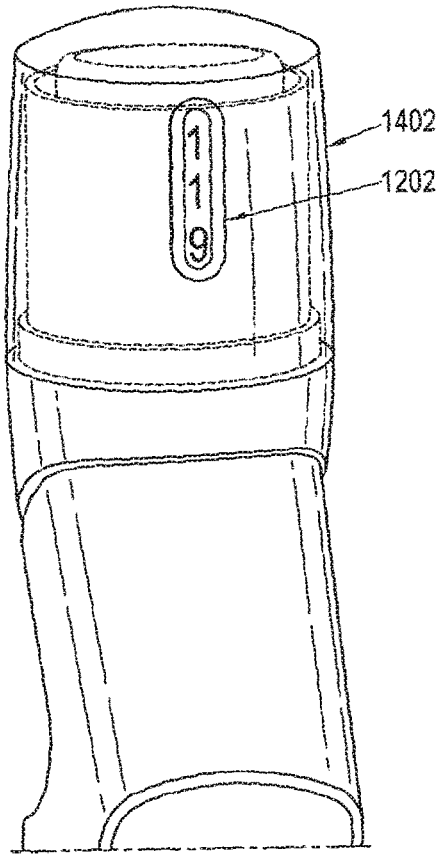
Fig.32 Amended
(PRIOR ART)
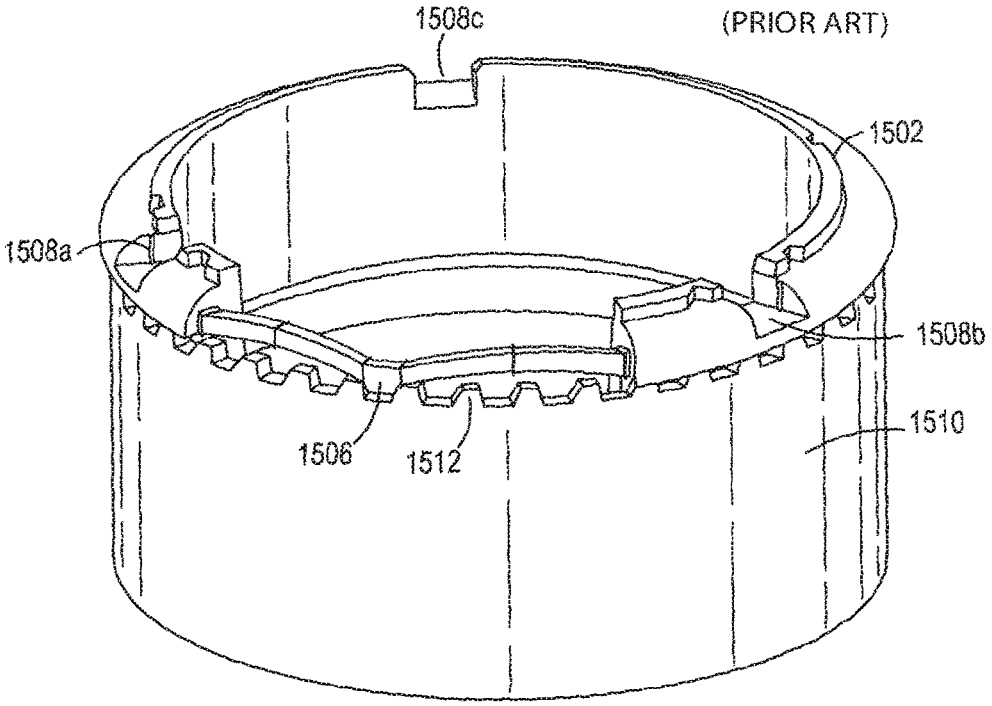
Fig.33a Amended
(PRIOR ART)

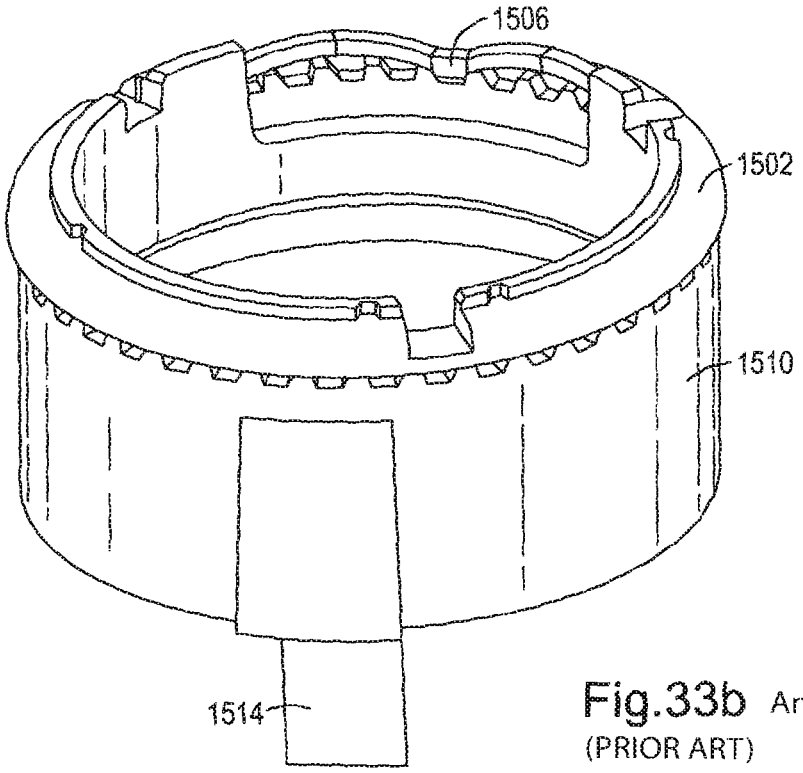
Fig.33b Amended
(PRIOR ART)
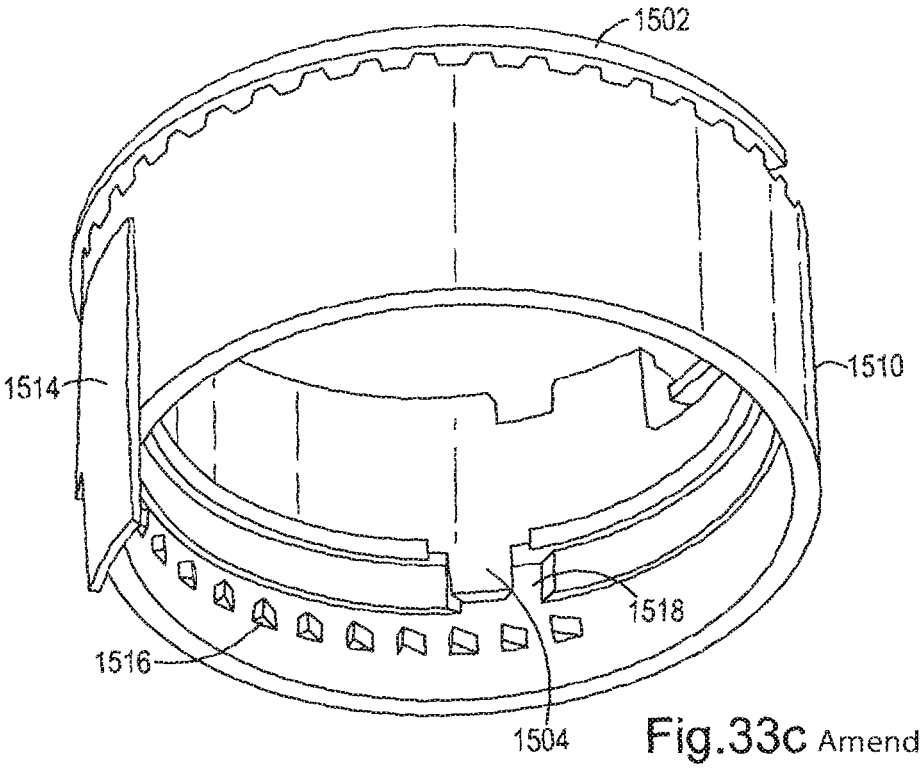
Fig.33c Amended
(PRIOR ART)

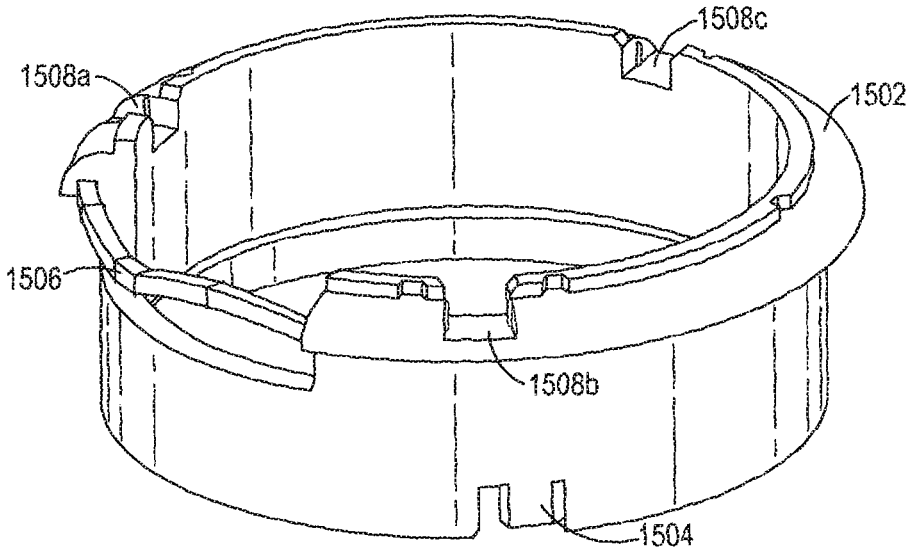
Fig.34a Amended
(PRIOR ART)
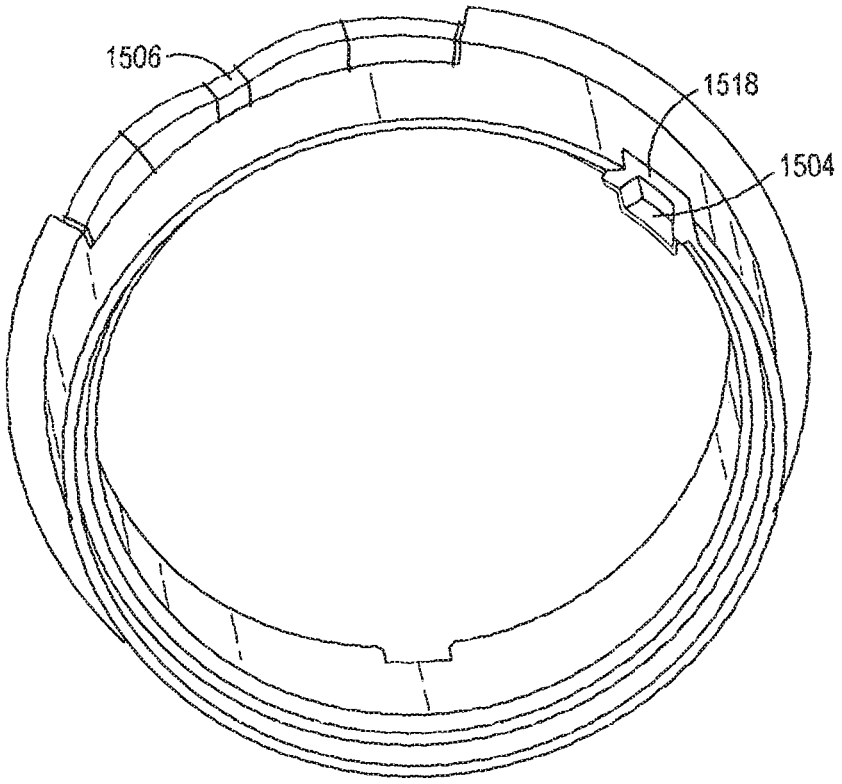
Fig.34b Amended
(PRIOR ART)

DISPENSER

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

FIELD OF THE INVENTION

The present invention relates to dispensers, in particular to dispensers for dispensing a dose of a gaseous, gas borne or droplet substance from a substance source and dispensers comprising dosage counters.

BACKGROUND OF THE INVENTION

In general, metered-dose inhalers (MDIs) are devices for dispensing medicaments, e.g. in aerosol form, to the lungs. Broadly speaking dispensers such as MDIs are comprised of two components: a container and a delivery device. The container holds the medication, e.g. dissolved or suspended in a propellant under high pressure to maintain a liquid phase. Additionally the container often comprises an internal metering valve, which is designed to release a precisely measured, reproducible dose of medicament when the valve is actuated. The delivery device typically includes an actuator and a mouthpiece. The actuator, which can be triggered by the user, for example by inhalation or manual operation, typically interacts with the metering valve of the container to induce release of a dose. The mouthpiece serves to direct the medication towards the user.

We have previously described a number of dispensers, see for example U.S. Pat. No. 7,721,731. We have also disclosed dosage counters for use with such dispensers, see for example WO 2010/103315. Further examples of dose counters and dispensers may be found in WO2005/060535, GB2372542 and US2011/259324.

It has been found that, during use of the dispenser and counter, manufacturing tolerances may in some instances affect the performance. As such, we have appreciated the need for an improved dispenser and an improved counter.

SUMMARY OF THE INVENTION

According to the invention there is provided a dispenser for dispensing a dose of a gaseous, gas borne or droplet substance from a substance source, the dispenser comprising: a body for receiving a substance source, the body having a mouthpiece; a junction member slideably arranged in the body for movement in a longitudinal axis of the body to release a dose of a substance from a substance source, the junction member comprising a socket for receiving a spout of a substance source; a dispenser driver for moving the junction member in the longitudinal axis of the body to release a dose of a substance from a substance source, the dispenser driver comprising a pivot shaft and a cam arranged on the shaft, the dispenser driver being arranged within the body such that rotation of the pivot shaft causes the cam to rotate and apply a force to the junction member so as to move the junction member in the longitudinal axis; and a cam follower slideably arranged within the body, the cam follower comprising a base and a substantially rigid protrusion extending from the base, the protrusion being arranged between the dispenser driver and the junction member such that a force applied by the cam of the dispenser driver to the protrusion causes the cam follower to slideably move in the longitudinal axis of the body and apply a force to the junction member so as to release a dose of a substance from a substance source.

The provision of a cam follower between the junction member and the cam provides more reliable longitudinal movement of the junction member within the body to effect release of a dose of a medicament from a medicament container. Since the protrusions are substantially rigid, the whole cam follower moves longitudinally up and down as the cam arrangement imparts an upward force on the protrusion. In prior versions (where tongues were anchored at one end to the main body part), the tongues would flex at the fixed end, and the tongues had tendencies to bend and buckle under the force. In the preferred embodiment, the protrusions remain rigidly in place and instead the cam follower slideably moves within the guide of the main body part. As such, this enables a more reliable longitudinal action of the junction member 41.

In embodiments, the body comprises a guide for guiding the slideable motion of the cam follower base in the longitudinal axis, the guide being shaped to receive the base of the cam follower in a slideable engagement. Preferably, the guide comprises one or more guide rails arranged and adapted to co-operate with one or more guide rails on the cam follower base such that the cam follower is slideable within the body.

In some embodiments, the cam follower further comprises a resiliently deformable clip disposed on a lower edge of the base for engaging with a correspondingly shaped protrusion in the body, and wherein, when the clip is engaged with the protrusion, the cam follower is retained in the longitudinal position in the body until a force is exerted on the cam follower by the cam. Such a clip aids assembly during manufacture of the dispenser, since the clip will maintain the cam follower in the correct position whilst other components are assembled around the cam follower.

In embodiments, the dispenser further comprises a pivotally mounted closure for the mouthpiece, the closure being coupled to the dispenser driver such that pivoting of the cover causes rotation of the pivot shaft of the dispenser driver.

In further embodiments, the dispenser further comprises: a breath actuatable valve incorporated with the junction member, for controlling the release of a gas and/or liquid comprising a substance, the valve comprising: a flexible tube for receiving a dose of a substance, the tube extending from an inlet end connected to the junction member socket, having a location which is kinkable for closure of the valve in a ready position and moveable to a release position in which the tube is un-kinked for opening of the valve, and having an outlet end moveable for kinking/un-kinking of the tube; and an outlet member carrying the outlet end of the flexible tube and pivotally connected to the junction member for control of kinking/un-kinking movement of the flexible tube; the tube being kinked to an obturating extent when the pivotal outlet member is in a ready position and un-kinked when the pivoted outlet member is moved to a release position. Preferably, the dispenser further comprises: a sear on the outlet member to hold the outlet member in the ready position prior to inhalation; a breath actuatable flap carried on the junction member and arranged for action of inhalation breath on it, the flap having: a latch complementary to the sear; the flap being arranged: to releasably receive the pivotal outlet member for kinked closure of the flexible tube by cooperation of the latch and the sear and to release the pivotal outlet member for un-kinking of the tube, and substance release, on inhalation, by release of the sear from the latch and movement to the release position of the outlet member.

In these further embodiments, the pivotal outlet member is arranged to move by the force arising from pressure in the kinked location and/or under the resilience of the kinked location itself. Furthermore, the junction member, the kink tube and the pivotal outlet member may be of an integral plastics material injection moulding, the pivotal outlet member being pivoted to the junction member by one or more living hinges and having an outlet nozzle held by the outlet member.

In embodiments, the flap has an integral spring acting on the junction member to bias it normally to an upward position in which the flap rests on an upper crown portion of the junction member. Furthermore, the flap may include a finger arranged to act on the pivoted outlet member to urge it towards its open position as the flap moves under the action of inhalation breath.

In embodiments, the dispenser may further comprise a dose counter for indicating a number of actuations of the dispenser corresponding to a number of doses dispensed from a substance source, or a number of doses remaining in a substance source.

Preferably, the dose counter comprises: a counter having indicia, the counter being rotatable within the body in increments about the longitudinal axis of the body; a counter driver for driving the counter, the counter driver being coupleable to the junction member and arranged to be reciprocatably moveable within the body in the longitudinal axis with the junction member; and a drive mechanism for rotating the counter, the drive mechanism being coupled to the counter driver and configured to rotate the counter in response to longitudinal movement of the counter driver.

Preferably, the body comprises a counter driver guide configured to guide the counter driver in the body so as to prevent rotation of the counter driver in the longitudinal axis. Preferably, the counter driver guide comprises a protrusion extending from the body, the protrusion being configured and shaped so as to co-operate with a correspondingly shaped notch in the counter driver.

The counter driver guide prevents the counter driver from rotating about the longitudinal axis. Since rotation of the counter driver about the longitudinal axis would cause the counter to mis-count (i.e. actuate when it should not, or not actuate when it should), the counter driver guide provides for a more reliable count action.

In embodiments, the junction member comprises one or more slots, and the counter driver comprises one or more protrusions for engaging with the junction member so as to couple the junction member and counter driver.

In preferred embodiments of the dispenser comprising the counter, the counter comprises a first ring member having first indicia and a second ring member having second indicia, each of said first and second ring members being rotatable in increments about the longitudinal axis, one or both of said first and second indicia indicating a count, and the dosage counter further comprises: a coupling mechanism for releasably coupling said first ring member to said second ring member, to allow said first and second ring members to rotate cooperatively when coupled and to allow independent rotating of said first ring member when not coupled. Preferably, the dispenser further comprises a third ring member being coaxially arranged about said longitudinal axis.

In embodiments having the third ring member, the third ring member comprises a limiting mechanism to limit free rotation of said second ring member relative to said third ring member about said common axis. Preferably, the limiting mechanism comprises a resiliently deformable portion for applying pressure on said second ring member for said limiting.

In embodiments, the second ring member comprises a plurality of substantially equally-spaced protrusions and wherein said limiting mechanism engages with said protrusions for limiting said free rotation of said second ring member.

In embodiments having the third ring member, the third ring member comprises one or more locating recesses disposed in an upper circumferential surface for engaging with correspondingly-shaped protrusions in a counter housing for preventing free rotation of said third ring member.

In some embodiments, the first and second indicia each comprise one or more of: numbers, colours, letters and symbols. Preferably, the first indicia comprise a first row of numbers, and said second indicia comprise a second and a third row of numbers. Preferably, the first row of numbers represents units digits, said second row represents tens digits, and said third row represents hundreds digits. In some embodiments, the first row of numbers comprises repeated sets of integers. Furthermore, in some embodiments, the second row of numbers comprises repeated sets of integers and said third row of numbers comprises a set of integers.

In embodiments, the second ring member comprises a display cover element for obscuring a view of said first indicia.

Furthermore, in some embodiments of the dispenser comprising the counter, at least part of said drive mechanism is integral with said first ring member.

Preferably, the drive mechanism of the counter comprises a pawl-and-teeth mechanism. And preferably, the pawl-and-teeth mechanism comprises: a first and second pawl engageable with a plurality of teeth, and wherein each of said first and second pawls comprise a driving engagement face for engaging in a driving engagement with one of said plurality of teeth, and a sliding engagement face for siding over one of said plurality of teeth.

In some embodiments having a pawl-and-teeth mechanism, each of said first and second pawls is arranged such that: said first pawl engages in a driving engagement with one of said plurality of teeth during a count stroke of said teeth, and said second pawl engages in a driving engagement with one of said plurality of teeth during a return stroke of said teeth.

Furthermore, each of said first and second pawls may be arranged such that: said second pawl rides over one of said plurality of teeth during said count stroke, and said first pawl rides over one of said plurality of teeth during said return stroke.

In further embodiments, said first and second pawls are integral with said first ring member, and said plurality of teeth are disposed on a teeth-bearing member arranged to be reciprocally moveable within the bore of said first ring member, and wherein said pawl-and-teeth mechanism is configured such that reciprocal movement of the teeth-bearing member within the bore of the first ring member causes rotational movement of the first ring member.

In some embodiments, the drive mechanism comprises third and fourth pawls engageable with the plurality of teeth, the third and fourth pawls being integral with the first ring member on a surface radially opposing the first and second pawls.

The present invention also provides a dispenser as described above in its various embodiments, further comprising a substance source. Preferably, the substance source is a pressurised metered-dose inhaler (pMDI).

The present invention also provides a dispenser for dispensing a dose of a gaseous, gas borne or droplet substance from a substance source, the dispenser comprising: a body for receiving a substance source, the body having a mouthpiece; and a dose counter for indicating a number of actuations of the dispenser corresponding to a number of doses dispensed from a substance source, or a number of doses remaining in a substance source, the dose counter comprising: a counter having indicia, the counter being rotatable within the body in increments about the longitudinal axis of the body; a counter driver for driving the counter, the counter driver being arranged to be reciprocatably moveable within the body in the longitudinal axis in response to an actuation of the dispenser; and a drive mechanism for rotating the counter, the drive mechanism being coupled to the counter driver and configured to rotate the counter in response to longitudinal movement of the counter driver, wherein the body comprises a counter driver guide configured to guide the counter driver in the body so as to prevent rotation of the counter driver in the longitudinal axis.

The counter driver guide prevents the counter driver from rotating about the longitudinal axis. Since rotation of the counter driver about the longitudinal axis would cause the counter to mis-count (i.e. actuate when it should not, or not actuate when it should), the counter driver guide provides for a more reliable count action.

In some embodiments of the dispenser, the counter driver guide comprises a protrusion extending from the body, the protrusion being configured and shaped so as to co-operate with a correspondingly shaped notch in the counter driver.

Furthermore, the dispenser may comprise a junction member slideably arranged in the body for movement in a longitudinal axis of the body to release a dose of a substance from a substance source, the junction member comprising a socket for receiving a spout of a substance source. In an embodiment comprising the junction member, the junction member may comprise one or more slots, and the counter driver comprises one or more protrusions for engaging with the junction member so as to couple the junction member and counter driver.

The present invention also provides a dispenser for dispensing a dose of a gaseous, gas borne or droplet substance from a substance source, the dispenser comprising: a body for receiving a substance source, the body having a mouthpiece; a junction member slideably arranged in the body for movement in a longitudinal axis of the body to release a dose of a substance from a substance source, the junction member comprising a socket for receiving a spout of a substance source; a dispenser driver for moving the junction member in the longitudinal axis of the body to release a dose of a substance from a substance source, the dispenser driver comprising a pivot shaft and a cam arranged on the shaft, the dispenser driver being arranged within the body such that rotation of the pivot shaft causes the cam to rotate and apply a force to the junction member so as to move the junction member in the longitudinal axis; a cam follower slideably arranged within the body, the cam follower comprising a base and a substantially rigid protrusion extending from the base, the protrusion being arranged between the dispenser driver and the junction member such that a force applied by the cam of the dispenser driver to the protrusion causes the cam follower to slideably move in the longitudinal axis of the body and apply a force to the junction member so as to release a dose of a substance from a substance source; and a dose counter for indicating a number of actuations of the dispenser corresponding to a number of doses dispensed from a substance source, or a number of doses remaining in a substance source, the dose counter comprising: a counter having indicia, the counter being rotatable within the body in increments about the longitudinal axis of the body; a counter driver for driving the counter, the counter driver being arranged to be reciprocatably moveable within the body in the longitudinal axis in response to an actuation of the dispenser; and a drive mechanism for rotating the counter, the drive mechanism being coupled to the counter driver and configured to rotate the counter in response to longitudinal movement of the counter driver, wherein the body comprises a counter driver guide configured to guide the counter driver in the body so as to prevent rotation of the counter driver in the longitudinal axis.

We shall now describe embodiments of the present invention, by way of example only, and with reference to the accompanying drawings, in which:

FIG. 1 is a perspective view of a dispenser according to the invention in closed position;

FIG. 2 is a similar view of the dispenser in open position;

FIG. 3 is a central cross-sectional view of the dispenser closed;

FIG. 4 is an exploded view of a prior version of the dispenser;

FIG. 5a is an inside, front view of a main body part of a prior version of the dispenser;

FIG. 5e is a cam follower component of a preferred embodiment of the dispenser;

FIG. 5f is a rear view of the cam follower of FIG. 5e;

FIG. 6 is an inside, rear, view of a cover of the dispenser;

FIG. 7 is an oblique view from the front and below of a front body part of the dispenser;

FIG. 8 is a view from the opposite direction of the front body part;

FIG. 9 is an oblique view from the front and below of a junction member of the dispenser (shown in a form after moulding, but prior to insertion into the main body part);

Figure 22C:
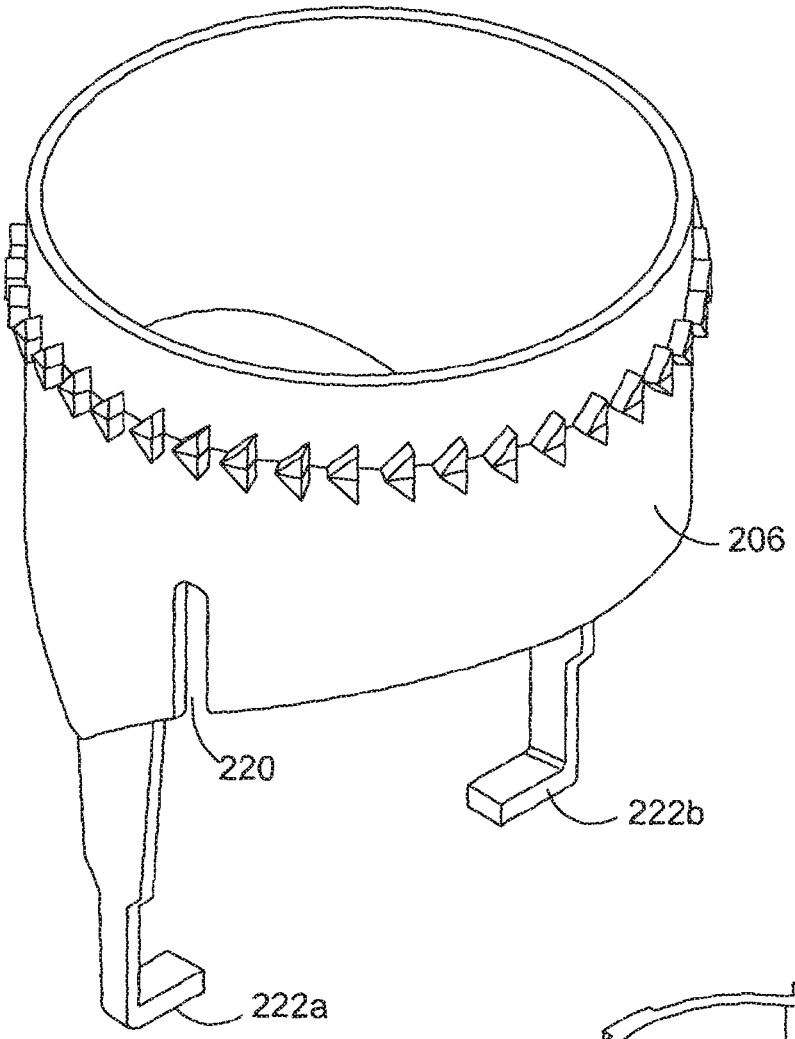
Figure 22D:
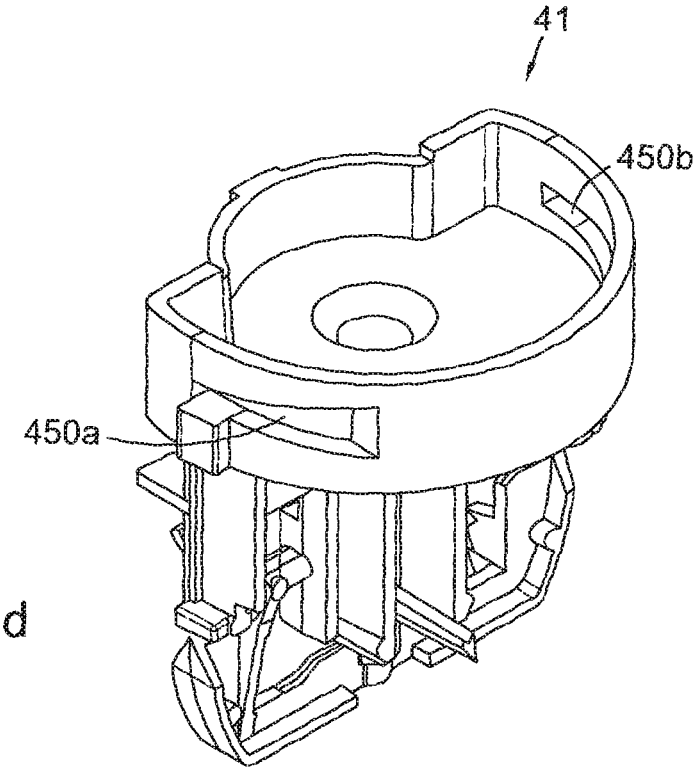
Figure 22E:
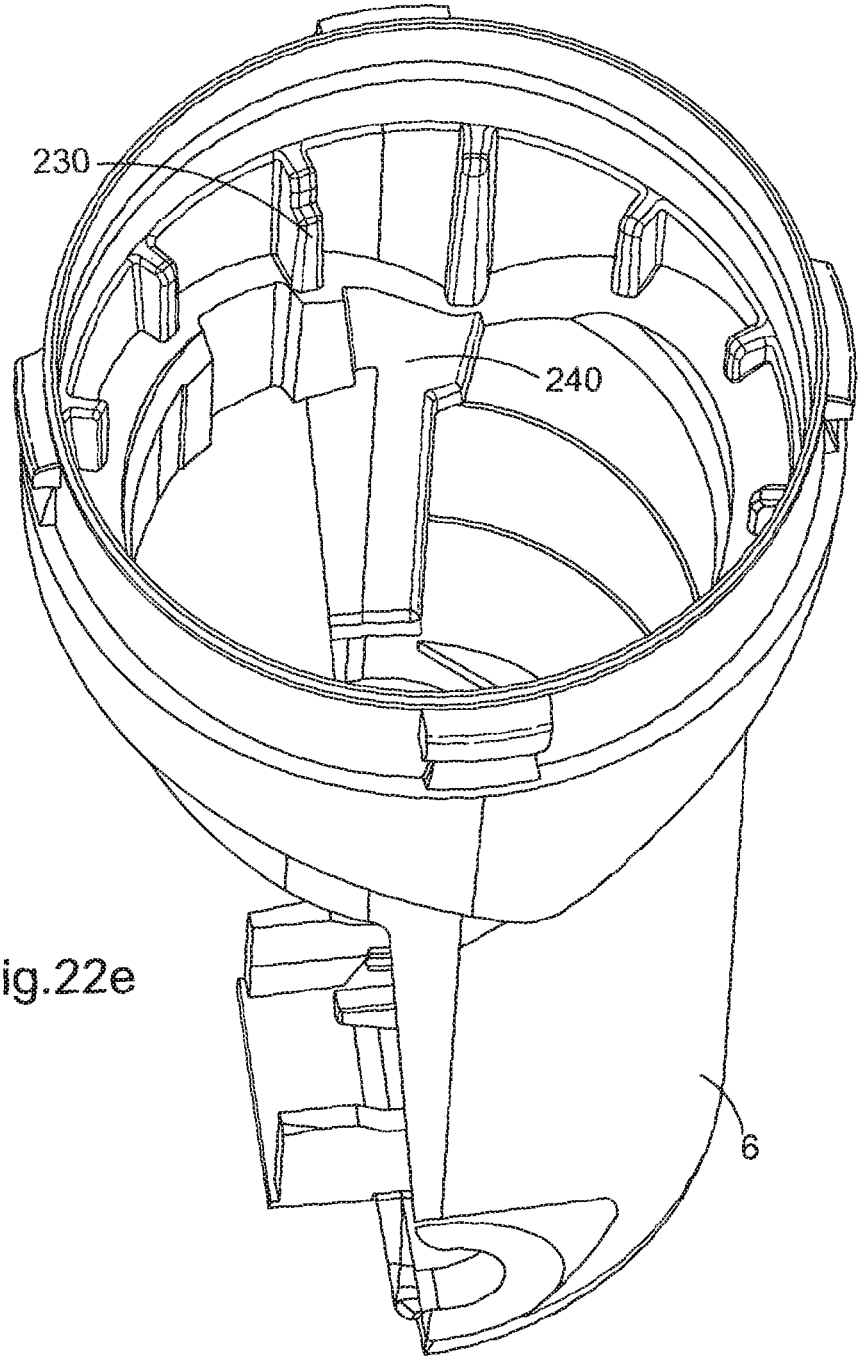

FIG. 10 a rear view of the junction member;

FIG. 11 is a cross-sectional side view of the junction member on the line A-A in FIG. 10;

FIG. 12 is a cross-sectional side view of the cover on line C-C in FIG. 6;

FIG. 13 is a central, cross-sectional side view of the cover on line B-B in FIG. 6;

FIG. 14 is a perspective view from behind of a flap of the dispenser;

FIG. 15 is a plan view of the flap;

FIG. 16 is a side view of the flap;

FIG. 17 is a series of scrap views of the flap and kink valve in the junction member illustrating operation of the valve;

FIG. 18a is a perspective view of a dispenser including a counter;

FIG. 18b is a perspective view of a dispenser including the counter;

FIGS. 19a and 19b show a drive mechanism for the counter;

FIGS. 20a to 20d are schematic diagrams showing a part of the principle of operation of the drive mechanism of the counter;

FIGS. 21a to 21d are schematic diagrams showing another part of the principle of operation of the drive mechanism of the counter;

FIGS. 22a and 22b show a preferred drive mechanism for the counter;

FIG. 22c shows a yoke (also known as a counter driver or teeth-bearing member) of a preferred embodiment of the counter;

FIG. 22d shows a junction member of a preferred embodiment of the dispenser;

FIG. 22e shows a top perspective view of a main body part for use with the yoke of FIG. 22c;

FIGS. 23a to 23d are schematic diagrams showing a part of the principle of operation of the preferred drive mechanism of the counter;

FIGS. 24a to 24d are schematic diagrams showing a part of the principle of operation of the preferred drive mechanism of the counter;

FIG. 25 is a perspective view of the counter;

FIG. 26 is a perspective view of a first ring member of the counter of FIG. 25;

FIG. 27 is a top view of the counter of FIG. 25;

FIGS. 28a to 28d schematically show in perspective view the operating principle of the counter;

FIGS. 29a to 29d schematically show from a top view the operating principle of the counter;

FIGS. 30a to 30c are schematic diagrams showing the principle of operation of the counter;

FIG. 31 is a perspective view of a dispenser including the counter;

FIG. 32 is a perspective view of a dispenser including the counter;

FIGS. 33a to 33c are perspective views of portions of the counter;

FIGS. 34a to 34b are perspective views of a third ring member of FIG. 33.

DETAILED DESCRIPTION OF THE PREFERRED EMBODIMENTS

Dispenser

Figure 5B:
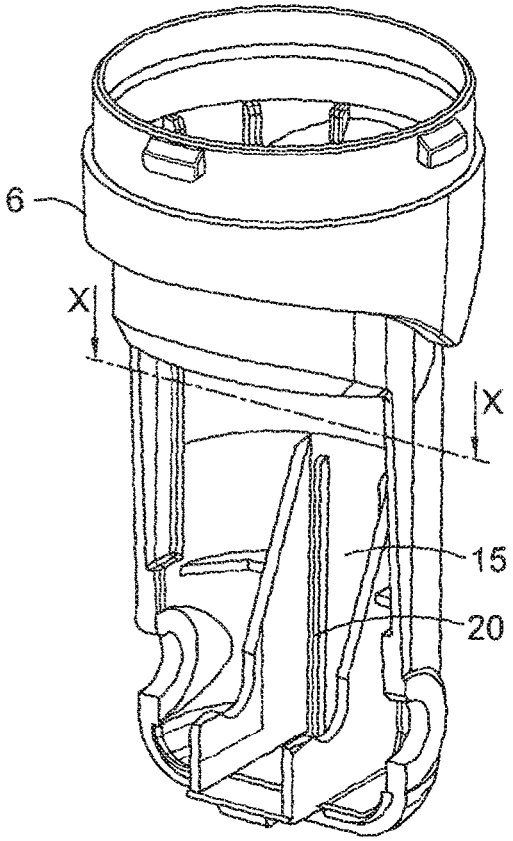
FIG. 5b is an inside, front view of a main body part of a preferred embodiment of the dispenser.
Figure 5D:
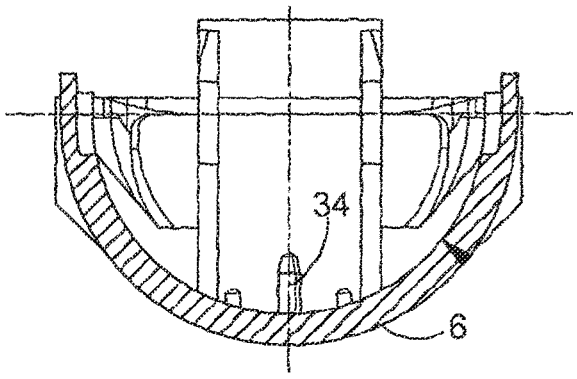
FIG. 5d is a cross-sectional view along line X-X of the main body part of FIG. 5b.
Figure 5C:
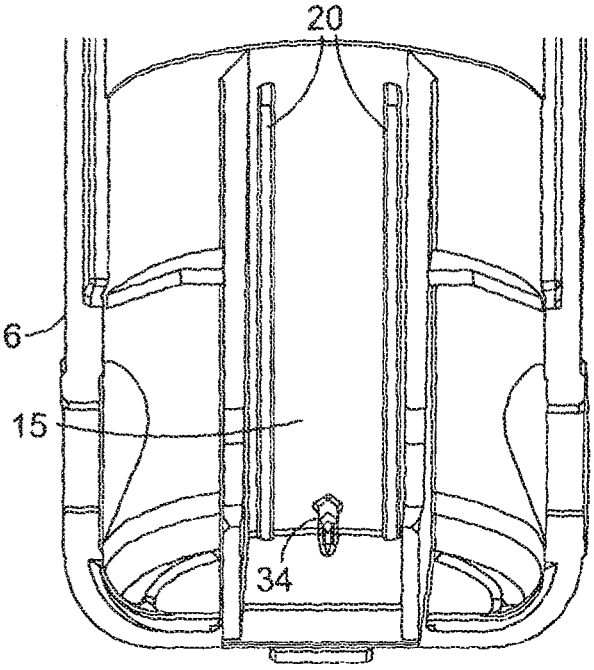
FIG. 5c is an inside, front view of a portion of the main body part shown in FIG. 5b.

Referring first to FIGS. 1 to 4 of the drawings, the dispenser has a body 1 with a mouthpiece 2 and a pivoted mouthpiece cover 3. The mouthpiece is formed as an aperture 4 in a separate body part 5 clipped to a main body part 6 (although the skilled reader would appreciate that this formation could be made using a single-moulded piece). The main part 6 has upper and lower formations 7,8 (see FIG. 5a) and the mouthpiece part has upper and lower complementary formations 9,10 (see FIG. 8) which engage when the mouthpiece part is slid from below to engage with the main part. The separate body part 5 has cutaway 11 with respect to the main body part 6, to define an air inlet 12 exposed by the cover 3 when this is opened. A medicament can C is fitted to the body part 6. Immediately within the air inlet 12 is a guard 13 against fingers. It is backed up by strengthening flanges 14, which additionally guard the cam mechanism to be described in the next paragraph.

Above the guard 13, a series of four ribs 151, 152 (in FIG. 7) extend and provide rigidity to the structure. The end ones 151 are longer and provide eventual stops for the flap of the actuation mechanism described below in the case of malfunction. The inner ones 152 act as flow restrictors to cause a pressure drop between the inlet 12 and the aperture 4 when the mechanism has been actuated, primarily to control the air flow rate through the device.

The cover 3—see FIGS. 6,12 & 13—is pivoted about an axis A low in the body 6 at the joint between the two body parts. Integrally moulded with the cover 3 is a C section shaft 21, via webs 22. The shaft carries a cam arrangement 23 (see FIG. 4), comprising two cam lobes 231 and 232, together with two fingers, a central one 24 and a outer one 25. The latter is integral with one of a pair of discs 26, between which are the cam lobes, the shaft is bearingly supported by part circular journals 27 in flanges 28 integrally moulded within the main body part 6 (see FIG. 5a). At the joint line between the two body parts 5 and 6 further coaxial scallops 29 are provided in the main body part 6 for the shaft 21.

The body parts 5,6, and the cover 3 (with the shaft and cam arrangement) in the described embodiments are of moulded polypropylene material, whereby they can be fitted together with a modicum of flexure.

The can C is held in an opening 31 at the upper end of the main body part 6, where the body part extends completely around a valve crimp portion CP of the can C.

Moulded inside the main body part, inwards of the opening are internal grooves 32 (FIG. 5a). A junction member 41—see FIGS. 9,10 & 11—is slidably accommodated in the body with the grooves 32 engaged by ribs 42 at its periphery. The junction member in this embodiment also is of moulded polypropylene. Centrally, the junction member has a socket 43 for accommodating a spout or an outlet stem S of the can C. The socket is continued by a flexible tube 44, which has a thin wall, kinkable location 45 and a nozzle end 46. This is in a movable outlet member 48 of the junction member. The main part 411 of the junction member 41 and the outlet member 48 are connected by a living hinge 49, in the form of two membranes 491,492 at respective sides of the junction member between lugs 561,562 and tabs 563,564. The tabs are interconnected by a bar 52 having the nozzle aperture 53. Between the lugs 561,562 and on either side of the kinkable location 45 extend two followers 541,542, which are integral with the respective lugs 561,562 and are acted on by the cam lobes 231,232 (see FIG. 6), with the interposition of tongues 551,552 extending from the inside of the main body part 6 to react lateral action on the junction member from the cam arrangement. The followers 541,542 have radiused portions 56, centred on the hinge axis, with upper and lower valve travel stops 571,572.

The lugs 561,562 carry on their sides facing the same direction as the radiused portions 56, pairs of pivot clips 581,582 for pivotally locating the flap to be described below. One the same side of moulding a pair of sears 591,592 are provided on the tabs 563,564.

It was found that the tongues 551, 552 extending from the inside of the main body part 6 did not always provide a reliable longitudinal action on the junction member (i.e. motion along the longitudinal axis of the main body part 6, that is along the long axis of the main body part), as the tongues often bent or buckled under the forces being applied by the cam. As such, the force from the cam on the tongues did not always translate into a sufficient longitudinal movement of the junction member, which affected the dispensing of the medicament from a medicament source, or the action of the counter (described below—the counter is driven by the motion of the junction member).

In order to overcome this problem, we propose the features shown in FIGS. 5b to 5f, which show a preferred embodiment of the main body part 6 comprising a guide 15 along a back wall of the main body part. Two guide rails 20 are provided in the guide, and a protrusion 34 is provided at a lower portion of the base (extending from the back wall of the main body part).

Into the guide sits a cam follower 16, having a base 17. Two substantially rigid protrusions 18a and 18b extend from the base 17. Two guide rails 19a, 19b are disposed on the rear of the base 17. The cam follower 16 slides longitudinally within the guide 15 of the main body part 6, with the guide rails 20 and 19a, 19b interacting to retain the cam follower 16 in the guide 15. The cam lobes 231, 232 contact the underside surface of the protrusions 18, 18b and the junction member sits atop the upper surface of the protrusions 18a, 18b. As such, the cam lobes indirectly can apply a force to the junction member via the cam follower.

Since the protrusions 18a, 18b are substantially rigid, the whole cam follower moves longitudinally up and down as the cam arrangement imparts an upward force on the protrusion. In the prior version (where tongues 551, 552 were anchored at one end to the main body part at anchor point 553), the tongues would flex at the fixed end, and the tongues had tendencies to bend and buckle under the force. In the preferred embodiment, the protrusions 18a, 18b remain rigidly in place and instead the cam follower slideably moves within the guide of the main body part. As such, this enables a more reliable longitudinal action of the junction member 41.

To aid with the manufacturing and assembling process, resiliently deformable clips 35 are disposed along the lower edge of the base of the cam follower. The clips are arranged to cooperate with the protrusion 34 in the main body part 6. During assembly, the cam follower is placed in the guide, and the resiliently deformable clips engage with the protrusion 34 in order to retain the cam follower in place (i.e. along the lower edge of the main body part). The clips and protrusion are configured such that the force generated by the cam as the mouthpiece is opened is much greater than the force which can be resisted by the clips. As such, the clips do not affect the operation of the cam follower during use.

The flap 61—see FIGS. 14,15 & 16—has a pivot axis B. At opposite ends of the axis, the flap has small thrust flanges 62, with pivot pins 60 set in from them. Inboard of the pins, two swellings 63 are formed. Each has a finger 64,65 extending obliquely down from it. One of the swellings has a spring loop 66 extending backwards, inwards and forwards again with its distal end 67 adjacent the swelling to which its proximal end 68 is attached. Set into the swellings 63 from the pins are apertures 69 formed from above and latches 70 extending below the apertures. These have latch surfaces 71 formed during moulding by projections through the apertures. The latches have cam surfaces 72. These are positioned so as to abut the sears 591,592 as the device is in the ready position. The sears then pass over the end of the cam surfaces and come to engage on the latch surfaces. The final feature of the flap is a tongue 73, which extends between the followers 541,542 to control air leakage as might otherwise occur.

The operation of the device will now be described.

Initially, the device is closed and the flexible members are relaxed. In others words the flap is in its upper, upstream position, as shown in FIGS. 3, 9 & 17 (1), and the outlet member 48 of the junction member is in its lower position. The flap is held in this position by its spring 66, bearing with it distal end 67 on an abutment 81 set in from the lug 562 and the flap 61 resting on crown 41a of the junction member. The outlet member 48 of the junction member is pivoted down, due to the tendency of the kinked location to straighten to its as moulded state. Its position is controlled by two fingers 82 projecting laterally from the bar 52 to abut with the cam lobes 231,232.

On opening of the cover, the cam lobes act via substantially rigid protrusions 18a, 18b of the cam follower 16 on the followers 541,542 of the junction member 41. The cam follower 16 slides within the guide 15 of the main body part 6, which lifts the junction member 41 against the internal spring (not shown) of the metering valve in the can, with displacement of stem S inwards of the can. As the cover 3 is rotated, the central finger 24 between the cam lobes engages with a notched projection 83 between the fingers 82 on the outlet member of the junction member. This action lifts the outlet member and closes the kinked location. Further lifting of the junction member opens the can's valve and a dose metered by the can's valve is released into the inlet end of the flexible tube. It is retained there by the kinked location acting as a closed valve.

Naturally, the dose is retained only whilst the outlet member 48 of the junction member is retained in the upper ready position to which it has been moved. This is achieved by the sears 591,592 running along the cam surfaces 72 and engaging with the latch surfaces 71. As the sears move into engagement, the latches 70 are moved back, rotating the flap down against the action of the spring 66. Once the sears clear the end of the cam surfaces, the spring urges the latches fully under the sears. There is clearance for the outlet member 48 to continue to pivot further, until the central finger 24 passes on out of engagement with the projection 83. The device is now ready for inhalation.

Breathing in through the mouthpiece causes an air flow down through the air inlet 12, exposed on opening of the cover, and impinging on the flap 61. The flap is forced down against the action of the spring 66, releasing the sears 591, 592. The kink tube tends to straighten under the action of its own resilience and the pressure of the retained dose; thus the outlet member straightens through flexing of the hinges 491, 492 and the dose is released through the nozzle into the mouthpiece for inhalation, the nozzle traversing the mouthpiece aperture 4 as the dose is released.

The geometrical arrangement of the flap and the outlet member 48 can be seen in FIG. 17. The pivot axis B of the flap is spaced from the pivot axis D of the hingeable part, with the point of engagement of the sears 591, 592 and latches 70 lying between parallel planes B' and D' passing through the axes B and D. The actual points of engagement lie to the flap side of a common plane P passing through the axes.

After use, the mouthpiece cover is closed. The rotation of the cam arrangement allows the junction member 41 to return down and the finger 24 passes the notched projection 83 as a result of cam surfaces on its reverse faces.

Should the kink tube have lost its resilience and be slow in opening, the finger 64, at the spring side of the flap pivot acts on a lug 85 moulded integrally with the outlet member's lug 563 and extending back past the hinge axis H. Thus the hingeable part is moved to its open position.

A further eventuality is closure of the mouthpiece cover without inhalation. In this event, the finger 65 is engaged by the finger 25 to deflect the flap to its position in which the outlet member releases the dose. The spring 66 returns the flap after this movement of it (which of course occurs on closure even if the dose has been released by inhalation). Thus the device is returned to its initial position in which the plastics material resilient features are relaxed.

All the components of the device (excluding the can) are moulded of polypropylene, with the exception of the flap, whose spring dictates use of acetal copolymer.

Counter

Counters are useful in a wide variety of applications, and are especially important in the field of medical dispensers where an accurate determination of the number of doses of medicament remaining in a medicament container might otherwise be difficult to obtain. An example of such a medical dispenser is a metered-dose inhaler.

As medicament containers are typically made of an opaque material such as aluminium, and may be housed entirely within a delivery device, it is generally not possible for a user to gauge effectively how many doses of medicament remain therein. This may result in a user prematurely discarding a MDI still containing doses of medicament or worse using the MDI beyond its recommended lifetime. Neither situation is desirable—the former is wasteful while the latter is potentially dangerous. Users sometimes shake MDIs to try to obtain a measure of whether any medicament is present therein, but this only provides a very crude qualitative measure of the container contents. It would not, for example, enable a user to distinguish between a container comprising enough medicament and propellant to form a dose and one comprising a quantity of medicament and propellant that is less than that needed to fill the metering valve. In other words, there is a risk that users overestimate the amount of medicament present in a container and mistakenly conclude that there is sufficient medicament remaining for another dose when in fact there is not. Additionally a user may not be provided with sufficient warning to obtain a replacement medicament container prior to the one in use running out.

It is therefore desirable to provide dispensers, e.g. inhalers, with a counter mechanism that enables a user to track how many doses have been dispensed therefrom and, complementarily, how many doses remain. Indeed, regulatory bodies such as the Food and Drug Administration (FDA) of the United States and the European Medicines Agency (EMEA) have issued guidelines encouraging the implementation of dose-counters (Food and Drug Administration, "Guidance for industry: integration of dose counting mechanisms into MDI drug products", 2003; European Agency for Evaluation of Medicinal Products, "Final guideline on the quality of inhalation and nasal products", 2005).

Dose counters can generally be classified according to the manner by which a 'count' is registered, these being mechanical counters comprised of a series of moving parts that respond to a movement or mechanical force resulting, for example, in a displacement of the container/housing; electronic counters having electrical circuitry to sense an event associated with an actuation such as sound, temperature or pressure change; and electro-mechanical counters which combine electrical and mechanical parts.

Some background prior art relating to dose counters includes: EP1169245 Dispensing Apparatus Comprising a Dosage Counting Device; PCT/GB97/03480 Inhaler Dose Counter; PCT/US1996/008418 Indicator Device Responsive to Axial Force; PCT/FR2004/001844 Improved Dose Indicator for Fluid Product Dispensing Device; GB2372542 Dosage Counting Device; PCT/CA04/001884 Indicating Device with Warning Dosage Indicator; PCT/US04/039926 Dose Counter for Dispensers; and U.S. Pat. No. 7,047,964 Dispenser for Medicament.

Other developments in the field of dose counters include Bang & Olufsen Medicom's 'Insulair' (Trade Mark) device, and the disclosures of: WO 98/056444 Dispenser with Doses Counter; WO 04/001664 Actuation Indicator for a Dispensing Device; WO 07/012854 Canister-Supported Rotating Ring Count Readout Assembly for a Metered Dose Inhaler; and DE 10061723 Zählwerk zum Zählen dosierter Abgaben flüssiger oder fester Produkte sowie Einrichtung zum dosierten Abgeben solcher Produkte.

Although such devices have provided the advantage of being able to provide some measure of the number of doses of medicament dispensed from a container and/or the number of doses remaining therein, there remains room for improvement. In particular it has proven difficult to provide dose counters that reliably "count" the release of medicament doses from containers. The difficulty encountered is that a relatively small movement, typically of the metering valve stem, needs to be detected and translated into a count. This difficulty is exacerbated by the fact that manufacturing tolerances in the length of medicament containers means they do not have a consistent length. At the same time, it is highly undesirable for any movements not to be counted since this will lead to the counter indicating a higher number of doses remaining than is actually the case. Moreover there is also regulatory pressure to minimise the number of false counts.

Additionally it is desirable that a counter, especially a medicament dose counter, display the count information in an easy to read form so it may be used by children and the elderly as well as adults. Naturally there is also a need that the counter can be manufactured at low cost.

Drive Mechanism

The term "drive mechanism" is to be interpreted broadly as any means by which the dispensing of a dose from the medicament container is linked to a count being made by the counter. In described embodiments the dispensing of a dose will involve a vertical movement, e.g. of junction member 41, as described earlier. In the described preferred embodiment, this vertical movement is translated into an incremental rotation that is counted. In other embodiments the vertical movement that is translated into an incremental rotation of a counter may be the movement of a medicament container.

FIGS. 18a and 18b schematically show a dispenser 200 having a counter 203 and a drive mechanism 205. The counter comprises a first ring member 201 and a second ring member 202. The drive mechanism 205 is a pawl-and-teeth mechanism having a pawl-bearing member 204 (not shown in FIG. 18b) and a teeth-bearing member 206 (partially hidden from view in FIG. 18b). In this particular embodiment, the teeth-bearing member 206 is a hollow cylinder integral with the first ring member 201. The pawl-bearing member 204 extends fully around the teeth-bearing member 206. The reverse configuration may also be used, i.e. the pawl bearing member 206 may be integral with the first ring member 201. This arrangement is shown in FIG. 22.

Two pawls 208 are defined by a cutaway portion of pawl-bearing member 204. The pawls operatively engage with a ring of teeth 210 moulded on an outwardly facing surface of the teeth-bearing member 206 by means of inwardly extending protrusions on the tips of the pawls, as will be described in more detail later. A pair of arms 212a, 212b extend downwardly from the pawl-bearing member on either side of the metering valve assembly. The arms can be spring-loaded against, or affixed to, an upper portion of a junction member (hidden from view). The junction member moves vertically when a dose is dispensed. Alternatively the arms can be spring-loaded against, or affixed to, a moving container, e.g. a moving medicament container.

The action of lifting the junction member (which causes the release of a dose from a pressurised medicament container 114) imparts an upward force on the pawl-bearing member 204 in a direction parallel to the vertical axis 214 of the dispenser 200. This results in frictional engagement between the pawl(s) and the teeth. In turn, the teeth-bearing member 206 and first ring member 201 are rotated (clockwise in this particular case) about the vertical axis 214 by an increment.

Once a dose is released and the mouthpiece cover is being closed or is closed, the junction and pawl-bearing members are able to move downwards to their original positions by, for example, an internal spring (not shown) of the medicament container. This downward movement also results in frictional engagement between the pawl-bearing and teeth-bearing members, resulting in a further clockwise rotation of members 206, 201 about the vertical axis 214 by an increment.

Taken together, these two increments of rotation define a "complete" incremental rotation of the first ring-like member 201 from a first to a second position.

FIG. 19a illustrates an exemplary drive mechanism 205 in which the ring of teeth 210 is disposed on an inwardly facing surface of the teeth-bearing member 206, with the pawl-bearing member 204 being disposed within its bore. It will be recognised that the pawl- and teeth-bearing members are in a reverse configuration compared to the configuration shown in FIGS. 18a and 18b, though the operating principle of the drive mechanism remains substantially the same.

Two pawls 402a, 402b, are integrally defined in the pawl-bearing member 204, by a cutaway portion of its body. Viewed from this perspective, each pawl extends toward the ring of teeth 210 in an annular plane of the pawl-bearing member 204, at about the same (but opposite) angle $\alpha$, $\beta$. The second (lower) pawl 402b is offset in a circumferential direction relative to the first (upper) pawl 402a. The pawls each have a root end and a free end. A lip 408a, 408b, protrudes radially outwardly from each of the free ends, to operatively engage with the teeth.

The valve stem 118 of the metering valve assembly inserts down through the clearance hole in the base of the pawl-bearing member 204 to rest on a shelf 410 in a stem block 412.

In operation, and viewed from this perspective, the pawl-bearing member 204 moves up and down, and rotates, relative to the teeth-bearing member 206. For convenience, the upward and downward movements of the pawl-bearing member 204 will be referred to as the 'count stroke' and 'return stroke', respectively. These terms are only used for convenience and are not to be construed as meaning that a count only occurs during the count stroke. It will be apparent to those skilled in the art (and from the following description) that a count may occur during the count stroke, return stroke or a combination of both strokes.

FIGS. 20a to 20d show a sequence of cross-sectional views of the drive mechanism during the count stroke. In FIG. 20a, the pawl-bearing member is at rest on the teeth by means of a protruding block 510. An upwardly directed force on the pawl-bearing member initially results in frictional engagement between the lip 408a of the first (upper) pawl 402a and a vertical face 512 of tooth 502. This action guides the pawl-bearing member substantially vertically upwards, until such a time as the lip 408b of the second (lower) pawl 402b engages with a lower, sloped face 514 of tooth 506 (FIG. 20b). This effects an upward diagonal movement, which proceeds until lip 408b reaches, and then surpasses, the apex 516 of tooth 506 (FIGS. 20c and 20d, respectively). At the same time, the first (upper) pawl 402a flexes slightly inwardly to allow lip 408a to pass over tooth 502 (FIG. 20c). Dashed arrows indicate the direction of movement.

FIGS. 21a to 21d show a sequence of cross-sectional views of the drive mechanism during the return stroke. Like elements to those of FIG. 20 are indicated by like reference numerals.

In FIG. 21a, which corresponds substantially to FIG. 20d, the lip 408a of the first (upper) pawl 402a moves vertically downwards until it frictionally engages with an upper, sloped face 518 of tooth 502, resulting in a downward diagonal movement. In FIG. 21b, the lip 408a has proceeded further down face 518, and block 510 now engages an upper, sloped face 520 of tooth 504. This time the second (lower) pawl 402b flexes slightly inwardly to allow lip 408b to pass over tooth 504. This proceeds until the pawl-bearing member again comes to rest on the teeth (FIGS. 21c and 21d). FIG. 21d corresponds substantially to FIG. 20a, but rotated by one tooth, i.e. from tooth 506 to tooth 504.

Referring to FIG. 19b, this shows a side profile of the pawls 402a and 402b and the lips 408a and 408b. Each lip comprises a driving engagement face 440, which contacts a tooth during a driving engagement of that lip 408. Each lip also comprises a sliding engagement face 430, which enables a lip 408 to contact and lift over a tooth without engaging the tooth. The large arrows denote the faces of the pawl lips that contact teeth during one of the strokes. The opposite faces (shown without arrows) contact teeth during the other stroke. The angle $\gamma$ (that is the angle of the slope of the sliding engagement face 430 of the lip with respect to a vertical axis in the figure) must be sufficiently large enough to enable the lip 408b lift away and ride over the teeth when lip 408a is engaged with a tooth (i.e. driving engagement face 440a is in contact with, and drivingly engaged with a tooth). An angle greater than 15° is preferred. If the angle is less than 15°, the pawl may not lift above the tooth.

FIG. 22a illustrates a preferred embodiment of the drive mechanism 205 in which the ring of teeth 210 is disposed on an outwardly facing surface of a teeth-bearing member 206, which is placed within the bore of the pawl-bearing member 204. In this embodiment, the teeth-bearing member is a yoke (also known as a counter driver), and the pawl-bearing member is the first ring (or units ring) of the counter.

Two pawls 402a, 402b, are integrally defined in the pawl-bearing member 204, by a cutaway portion of its body. Viewed from this perspective, each pawl comprises two arms extending toward the ring of teeth 210 in an annular plane of the pawl-bearing member 204. The second pawl 402b is offset in a circumferential direction relative to the first pawl 402a. A lip 408a, 408b, protrudes radially outwardly from the point at which the two arms meet, to operatively engage with the teeth.

FIG. 22b shows a side profile of the pawls 402a, 402b. The numerals of FIG. 19b refer to like features of FIG. 22b. As with FIG. 19b, the angle $\gamma$ (i.e. the angle of the sliding engagement face 430 from the vertical of the drawing) must be sufficiently large enough to enable the sliding engaging face 430 to lift up and ride over the tooth (not shown). For example, the angle is preferably larger than 15°. More preferably, the angle is approximately 45°. It will also be noted that the orientation of the first pawl 402a is reversed to that shown in FIG. 19b. It will be appreciated that the engaged pawl (i.e. the pawl in driving engagement with the tooth) experiences a compression force that forces the pawl towards the toothed surface during engagement.

In operation, and viewed from this perspective, the teeth-bearing member 206 moves up and down (driven by the actuation of the junction member as described above), causing the pawl-bearing member 204 to rotate relative to the teeth-bearing member 206. For convenience, the upward and downward movements of the teeth-bearing member 206 will be referred to as the 'count stroke' and 'return stroke', respectively.

In preferred embodiment of the counter, the pawl-bearing member (i.e. the first ring member, or units ring of the counter) is provided with two sets of pawls, located substantially 180° apart around the pawl-bearing member. The second set of pawls is not shown in FIG. 22a.

FIG. 22c shows a yoke 206 (or teeth-bearing member or counter driver) according to preferred embodiments of the counter. In this preferred embodiment, the yoke comprises a notched portion 220, which is shaped and dimensioned to slideably engage with correspondingly shaped protrusions (230) on the inside of the main body part 6 (see FIG. 22e). Only one protrusion 230 is shown in the figure. In preferred embodiments, a second protrusion is positioned on the inside surface opposite protrusion or rail 230, which corresponds with an appropriately positioned notch on the yoke 206. These notches and protrusions allow the yoke to longitudinally move within the main body and prevents the yoke from rotating in the same axis of the counter rings. As such, this provides a more reliable count, as there is no rotational movement of the yoke (which would cause the counter mechanism to over count or under count). Whilst we describe feature 230 as a protrusion, the feature may also be considered a rail. FIG. 22e also shows a recess 240, into which the arms of the yoke 206 are slideably arranged to allow movement in the longitudinal axis of the main body part 6.

The preferred yoke 206 is also provided with protrusions 222a and 222b, which are shaped to engage with correspondingly shaped holes 450a and 450b in the junction member 41 (see FIG. 22d). In such embodiment, the yoke is coupled to the junction member via the protrusions and holes such that longitudinal motion of the junction member produces longitudinal motion of the yoke (which in turn drives the counter mechanism).

Figure 23A:
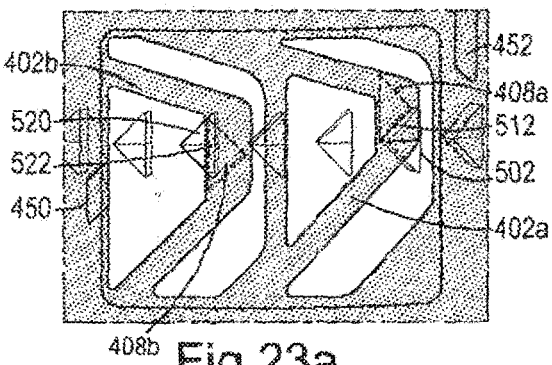
Fig.23a (PRIOR ART)

FIGS. 23a to 23d show a sequence of cross-sectional views of the preferred drive mechanism during the count stroke. In FIG. 23a, the teeth- and pawl-bearing members are at rest. An anti-slip bar 450, comprising a protrusion extending from the inner surface of the pawl-bearing member, is in an engaged position that is sufficiently in line with the teeth to prevent non-count rotation of the pawl-bearing member (i.e. rotation of the pawl-bearing member in an opposite direction to that of the pawl-bearing member during a count). The ant-slip bar 450 is configured to prevent relative rotation between the teeth-bearing member and pawl-bearing member in a non-count direction by blocking motion of the pawl-bearing member. The bar extends sufficiently from the inner surface of the pawl-bearing to hit one of the teeth, but not the outer surface of the teeth-bearing member.

An upwardly directed force on the teeth-bearing member initially results in an edge of the lip 408a coming into frictional engagement with a sloped face 512 of tooth 502 and moves the anti-slip bar 450 out of the path of the teeth to permit rotation. Further upward movement of the teeth-bearing member causes rotational movement of the pawl-bearing member (towards the left of the figure). At the same time, the inner non-vertical surface of lip 408b (shown as the arrowed surface in FIG. 22b) contacts a vertical non-leading edge 522 of tooth 520, which causes the pawl 402b to lift away from the plane of the teeth, and permits the pawl 402b to ride over the tooth without engagement.

Rotational movement of the pawl-bearing member continues until lip 408a and surface 512 no longer contact. At this point, lip 408b has cleared tooth 520, and falls back to the plane of the teeth by virtue of the pawl arms being resiliently deformable. Further upward motion of the teeth-bearing member has no further effect on rotation of the pawl-bearing member. However, a second anti-slip bar 452 (configured similarly to anti-slip bar 450) is brought into the path of the teeth to prevent backward (i.e. non-count) rotation of the pawl-bearing member.

FIGS. 24a to 24d show a sequence of cross-sectional views of the drive mechanism during the return stroke. Like elements to those of FIG. 23 are indicated by like reference numerals.

Figure 24A:
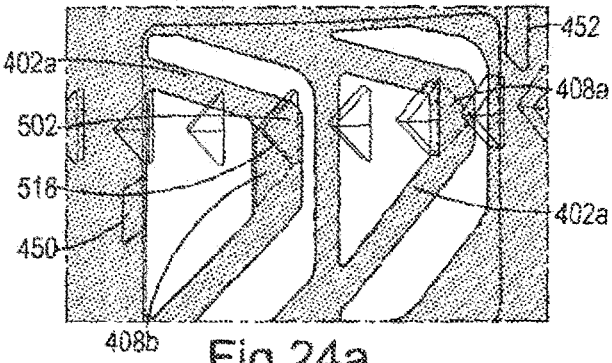
Fig.24a (PRIOR ART)
Figure 23B:
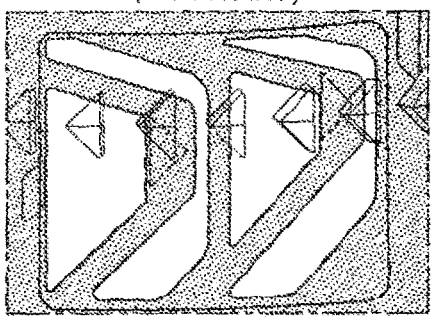
Fig.23b (PRIOR ART)
Figure 24B:
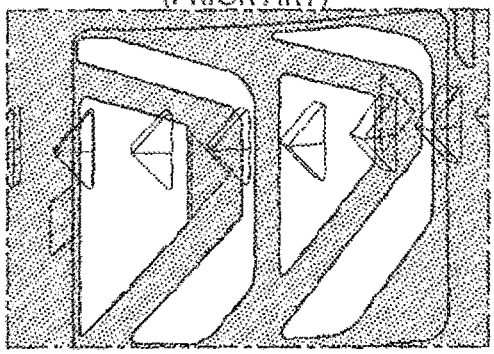
Fig.24b (PRIOR ART)
Figure 23C:
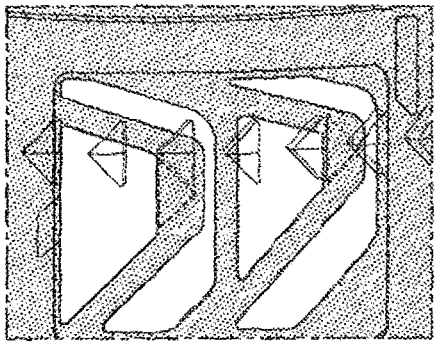
Fig.23c (PRIOR ART)
Figure 24C:
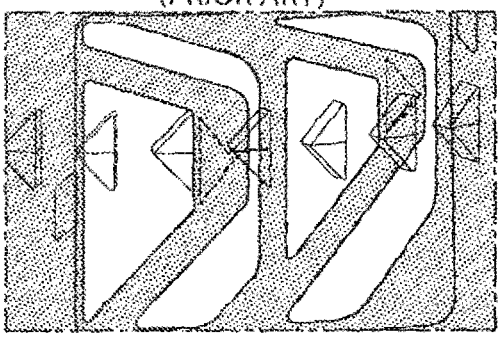
Fig.24c (PRIOR ART)
Figure 23D:
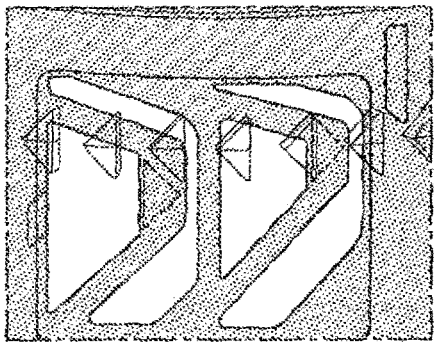
Fig.23d (PRIOR ART)
Figure 24D:
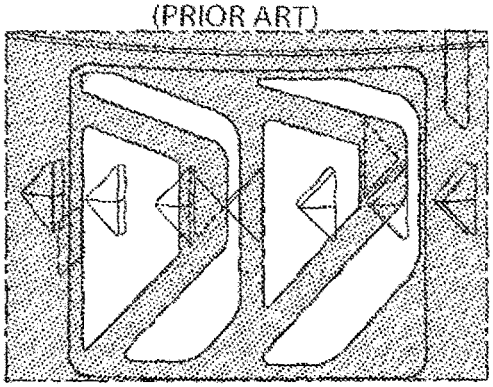
Fig.24d (PRIOR ART)

In FIG. 24a, which substantially follows FIG. 23d, the teeth-bearing member is lowered until lip 408b of the first pawl 402b frictionally engages with a lower, sloped face 518 of tooth 502 (simultaneously, the second anti-slip bar 452 is moved from the path of the teeth). Further downward movement of the teeth-bearing member causes rotational movement of the pawl-bearing member by virtue of the face 518 and lip 408a being frictionally engaged.

Face 518 proceeds further down lip 408b. At the same time, the inner non-vertical surface of lip 408a contacts a vertical non-leading edge of a tooth, which causes the pawl 402a to lift away from the plane of the teeth, and permits the pawl 402a to ride over the tooth without engagement.

Rotational movement of the pawl-bearing member continues until lip 408b and surface 518 no longer contact. At this point, lip 408a has cleared the tooth over which it was riding, and falls back to the plane of the teeth by virtue of the pawl arms being resiliently deformable. Further downward motion of the teeth-bearing member has no further effect on rotation of the pawl-bearing member. However, the first anti-slip bar 450 is brought back into the path of the teeth to prevent backward rotation of the pawl-bearing member.

Although the foregoing discussion describes the case where the pawl-bearing member rotates about an axis (i.e. rotates relative to the dispenser as a whole), it is equally possible that the teeth-bearing member rotates. Naturally it is also possible that the teeth could point in either direction around the circumference of the teeth bearing member.

It will be appreciated that a rotational displacement need not be performed by way of two engagements (though this may be beneficial), nor need it comprise vertical and rotational movement. For example, a drive mechanism providing purely rotational motion, in other words without vertical movement, could also be used.

Counter

FIGS. 25 to 34 provide various depictions of the counter in more detail.

Turning first to FIG. 25, the counter 205 is comprised of first ring member 201 and second ring member 202. The ring members are rotatably and coaxially arranged about the central axis 214, encircling the container of the dispenser. The second ring member is arranged substantially flush on top of the first ring member, with their outer circumferential surfaces being aligned so as to form a substantially continuous surface interrupted only by a hairline 720 where the two ring members meet. A pawl-bearing member 205 of a drive mechanism is integral with the first ring member 201.

A first row of numbers 701 ('8', '9', '0', '1') is displayed on the first ring member 201, with a second row of numbers 702 ('0', '1', '2', '3', '4',) and a third row of numbers 703 ('1', '1', '1') displayed on the second ring member 202. For clarity, only some of the numbers are depicted. A coupling mechanism 700 comprising an arm 704, a series of equally spaced protrusions 705, and a deflector 1002 can also be seen. The coupling mechanism allows the first ring member 201 to be coupled to the second ring member 202, so that they can be rotated in tandem by the drive mechanism when coupled, as detailed below. The spaced apart protrusions 705 are formed on an inner surface of the second ring member 202, and in this particular case extend only half way around the axis.

It will become clear in due course that, depending on the counting scheme used, multiple arms and/or deflectors may be provided. However, for purposes of clarity only, only one arm and/or deflector is depicted in these figures.

Referring now to FIG. 26, the arm 704 is integrally formed with an annular band 802 that sits in a recess of an upper radial surface 804 of the first ring member 201. Alternatively, the arm 704 can be directly mounted on, or integral with, upper radial surface 804. The arm 704 has a slotted body 712 which extends arcuately with approximately the same curvature of first ring member 201, and an upwardly extending contact end 710.

With reference to FIG. 27, being a view of FIG. 25 from above, the second ring member 202 (shown as a shaded ring) is slidably mounted on an outer portion of the upper radial surface 804 of the first ring member (shown as a blank ring, part of which is hidden from view underneath the shaded ring). From this perspective, it is apparent that the thickness of the second ring member 202, designated 't2', is about a third of the thickness of the first ring member 201, designated 't1'. The thickness of the first ring member 201 may be consistent along its height or it may be tapered, it being thickest at its upper radial surface 804. The dashed line represents an imaginary boundary line between the arm 704 and the spaced apart protrusions 705 formed on the inner surface 902 of the second ring member 202.

FIGS. 28 and 29 show, in a series of corresponding perspective and downward views respectively, the operation of the coupling mechanism.

FIGS. 28a and 29a show the arm 704 at a distance from the deflector 1002. In FIGS. 28b and 29b, the first ring member 201 and arm 704 are rotated in an anticlockwise direction, so that the upwardly extending contact end 710 of the arm 704 approaches the deflector 1002. The deflector 1002 is fixed to the container, or alternatively to an upper portion of a housing of the dispenser and/or to a sleeve surrounding the container. The deflector extends downwardly only to such an extent that the body 712 of the arm is allowed to pass underneath unimpeded.

As the contact end 710 reaches an inclined face 1004 of the deflector 1002, the arm 704 is deflected outwards (FIGS. 28c and 29c). At this point a trailing end 718 of the slot 714 catches one of the teeth 1102, thereby causing the second ring member 202 to be pulled along. When the contact end descends down face 1006 of the deflector, the tooth 1102 is released by the trailing end of the slot and the arm returns to its non-flexed position (FIGS. 29d and 29d). As seen in FIG. 29b, the upwardly extending contact end 710 of the arm 704 may have a face 720 complementing the inclined face 1004 of the deflector 1002, to allow for a smooth deflection. Preferably the contact end 710 is chamfered so that when it reaches the apex of deflector 1002, the arm can immediately begin to return to its non-flexed position.

As shown herein, the slot 714 forms an engaging portion of the arm 704, but it is recognized that any suitable engaging means could be used such as a hook. Accordingly, recesses could be formed in the second ring instead of protrusions.

The arm 704 is sufficiently flexible to permit a radially outward deflection (that is, towards the protrusions) when encouraged to do so, but also resilient enough to return to its original position. The counter may additionally comprise a second deflector that functions to move or deflect the engagement means (e.g. arm 704) back to its non-flexed position. This second deflector may, for example, be fixed to, or integral with, an inner surface of the second ring member 202. Whilst the second ring member is preferably slidably mounted on the first ring member, the second ring member is configured to resist rotation when there is no engagement between the arm and the teeth. For example, the second ring member comprises engagement features that engage with corresponding features on a dispenser cap, or a third ring member (described below) is employed.

An exemplary counting scheme for a counter configured for 200 doses is now described with reference to FIGS. 30a to 30c, which show the first and second ring members in three different display positions. For convenience, the ring members 201, 202 are shown as flat rings. Also shown in stylised form are the protrusions 705, the deflector 1002, a window 1202 through which the counter can viewed, and a display cover element 1204.

In this particular scheme, the first ring member 201 has a first row of numbers comprising four repeated sets of consecutive integers '0' to '9', i.e.:

0123456789012345678901234567890123456789.

Each set of integers covers a quarter turn of the first ring member 201, and here represents the 'units' digits of a count.

The second ring member 202 has second and a third rows of numbers. The second row comprises two repeated sets of consecutive integers '1' to '9' separated by a '0', while the third row comprises ten '1's optionally followed by a '2', e.g.:

11111111112

12345678901234567890

Similarly, each set of integers of the second and third rows covers a quarter turn of the second ring member 202. Here, the second row represents 'tens' digits, and the third row represent 'hundreds' digits of a count. Also shown on the second ring is a warning symbol in the form of an exclamation mark '!'.

In practice it may be more convenient to start a count at say '199' rather than '200', to avoid having to rotate the second ring member 202 initially. The integers forming the number '200' seen to the right of the window 1202 in FIG. 30a may therefore be omitted. Thus, when the first and second ring members are initially aligned in a housing of the dispenser, the first, second and third rows cooperatively display the number '199' (when read from top to bottom):

----------1111111111

----------01234567890123456789

0123456789012345678901234567890123456789 where '-' indicates a blank space.

For each of the first nine dispensed doses, the first ring member is rotated anticlockwise by an increment, i.e. counting down from '9' to '0', until the number '190' is displayed. Then for the tenth dispensed dose, the first and second ring members are coupled by means of the coupling mechanism so that the ring members are rotated in tandem by an increment. This results in the number '189' being displayed through window 1202. For the subsequent nine dispensed doses, the first ring member is again rotated anticlockwise by increments until the number '180' is displayed. For the twentieth dispensed dose, the coupling mechanism is again engaged, so that the first and second ring members are rotated in tandem by an increment and the number '179' is displayed through the window 1202.

FIG. 30b shows an intermediate count position, in which the number '72' is displayed. In this position, the third row has run out and a blank space appears instead. Alternatively, the blank space may be filled with indicia other than numbers, such as colours.

As the container becomes exhausted, e.g. below ten doses remaining, the second row of numbers can be replaced by an exclamation marks '!' or other warning indicators. Preferred warning indicators for this purpose are colours (e.g. red). Once the final dose has been dispensed (FIG. 30c), a cover element 1204 that is preferably attached to the second ring member and has therefore rotated at the same rate, is aligned with the window 1202. This occludes from view any indicia. The cover may have the word 'EMPTY' written on it for example.

Further actuations of the dispenser may still result in the first ring member 201 being rotated. However, since the teeth are disposed only half way around the second ring member 202, the coupling mechanism can no longer be engaged, i.e. there are no teeth for the slot of the arm to engage with. Thus, no further rotations of the second ring member 202 can be effected, so that the display cover element 1204 remains in place even if the first ring is still rotated by further actuations of the dispenser.

Thus viewed from a still further aspect the present invention provides a ring member for use in a counter having indicia and carrying protrusions that are disposed only partially around said ring member. Preferably the protrusions are disposed on the inner surface of the ring member.

In preferred embodiments the protrusions (e.g. teeth) are equally spaced apart. Particularly preferably the protrusions only extend three quarters of the way (e.g. about 270°) around the ring member, still more preferably the protrusions only extend between a quarter and half way (e.g. about 90°, 108° or 180°, or any angle therebetween) around the ring member.

It will be apparent that the number of deflectors and/or arms (not shown in FIG. 30) will depend on the implemented counting scheme. In FIG. 30 for example, where the first ring member 201 has a first row of numbers comprising four repeated sets of consecutive integers '0' to '9' such that each set covers a quarter turn of the first ring member 201, and where one deflector 1002 is provided, the counter will have four arms spaced at 90 degree intervals. Of course, other configurations will also be possible. For example, where the first ring member 201 has a first row of numbers comprising two repeated sets of consecutive integers '0' to '9' such that each set covers half a turn of the first ring member 201, and where one deflector 1002 is provided, the counter will have two arms spaced at 180 degree intervals. Alternatively, it may be possible to have a single arm and multiple deflectors 1002 spaced at intervals, or multiple arms and deflectors and multiple sets of teeth.

FIGS. 31 and 32 are perspective views of a dispenser including the counter. In contrast to FIGS. 18a and 18b, the pawl-bearing member rather than the teeth-bearing member is integral with the first ring member 201. This is for illustration purposes only. As discussed above, the preferred embodiment of the drive mechanism is shown in FIG. 22. Also visible in FIG. 31 is a strip of colour following the third row of numbers 703. FIG. 32 shows how a count ('119') can be viewed through a window 1202 of a housing 1402 of the dispenser.

FIGS. 33a to 33c show part of a preferred embodiment of the counter. In this preferred embodiment, the second ring member 1510 is rotatably and coaxially arranged with a first ring member 201 about a central axis 214 as described above (and as shown in FIGS. 25 and 26). For clarity, the first ring member 201 is not shown in these drawings.

As with the embodiments described above, the second ring member is arranged substantially flush on top of the first ring member, with their outer circumferential surfaces being aligned so as to form a substantially continuous surface interrupted only by a hairline where the two ring members meet. A pawl-bearing member 205 of a drive mechanism is integral with the first ring member 201.

In this preferred embodiment, the counter further comprises a third ring member 1502 that is coaxially arranged with the second ring member 1510. In use, the third ring member does not rotate. The third ring member comprises a deflector 1504 to deflect arm 704 on the first ring member 201 to engage with protrusions 1516 on the inside surface of the second ring member 1510 in the manner as described above with reference to FIGS. 28 and 29. As can be seen, the third ring member has a gap 1518 in its outer wall to enable the arm 704 to deflect outwards. A sloped edge on the trailing boundary of the window 1518 engages with an edge of the arm 704 to push the arm 704 away from the teeth 1516 after the arm has engaged with the teeth 1516. This ensures that unwanted further engagement of the tens (second) ring (which would lead to an incorrect dosage value being displayed) does not happen.

The third ring member 1502 further comprises a limiting mechanism 1506 which comprises a flexible and resiliently deformable portion that applies pressure to an upper circumferential surface of the second ring member 1510. The limiting mechanism limits the amount of rotation of the second ring member relative to the third ring member. More specifically, the limiting mechanism prevents the second ring member incorrectly rotating by two protrusions (or counts) in the event that the arm fails to decouple properly. In this embodiment, the second ring member 1510 also comprises a plurality of protrusions 1512 on an upper circumferential surface to engage with the limiting mechanism 1506 of the third ring member 1502. Preferably, protrusions 1512 are substantially equally-spaced. More preferably, the protrusions 1512 have substantially the same spacing as protrusions 1516 on the inside surface of the second ring member.

As described above with reference to FIGS. 28 and 29, when the first and second ring members are coupled, the second ring member rotates at the same rate as the first ring member (until the first and second ring members become uncoupled). By spacing the protrusions 1512 at substantially the same distance as protrusions 1516 (which form part of the coupling mechanism between the first and second ring members), this prevents the second ring member rotating further than is desired even if the arm does not properly decouple, which would indicate an incorrect count.

Furthermore, the third ring member also comprises a plurality of locating recesses 1508a, 1508b and 1508c in the upper circumferential surface. In preferred embodiments, correspondingly-shaped protrusions locate within these recesses to hold the third ring member in place and therefore to prevent rotation of the third ring member. The protrusions may be located in a container or a dispenser (e.g. in a dispenser cap). By preventing the third ring member from rotation, this ensures that the deflector 1504 remains in a consistent position relative to the first and second ring members.

A plurality of corresponding-shaped protrusions located in a container or dispenser may be designed with an asymmetrical pattern to provide a keying function. That is, the third ring member will only locate in one rotational position relative to the container and dispenser, and therefore also the first and second ring members. This ensures that the third ring member is always located correctly with respect to the first and second ring members to allow the count to correctly register.

The second ring member 1510 further comprises a display cover element 1514 for obscuring a view of the first indicia (as described above with reference to FIG. 30) to indicate that the counter has reached zero, indicating an empty dispenser.

FIGS. 34a and 34b show the third ring member without the second ring member. The reference numerals correspond with those in FIG. 33.

It will be apparent that the third ring member does not comprise indicia, and it is not intended to carry indicia, as this embodiment requires the third ring member to remain in a fixed rotational position relative to the first and second ring members for the count to indicate the correct remaining doses.

In all embodiments, the components are preferably made from polypropylene, except for the flap and cam follower, which are preferably made from acetal copolymer.

While the invention has been exemplified by the above description of specific embodiments, and uses thereof, the foregoing should not be considered by the reader as a limitation on the scope of the invention, which is defined in the appended claims.

Whilst the cam follower, counter driver guide and counter have been disclosed in combination in a single dispenser, it will be appreciated by the skilled reader that each of the cam follower, counter driver guide and counter need not all be present in the same dispenser and could be used in a dispenser without the other features being present. For example, the cam follower can be used in a dispenser without the counter driver guide and counter, and likewise with the counter driver guide and counter.

The invention claimed is:

1. A dispenser for dispensing a dose of a gaseous, gas borne or droplet substance from a substance source, the dispenser comprising:

a body for receiving the substance source, the body having a mouthpiece;

a junction member slideably arranged in the body for movement in a longitudinal axis of the body to release a dose of the substance from the substance source, the junction member comprising a socket for receiving a spout of the substance source;

a dispenser driver for moving the junction member in the longitudinal axis of the body to release a dose of the substance from the substance source, the dispenser driver comprising a pivot shaft and a cam arranged on the shaft, the dispenser driver being arranged within the body such that rotation of the pivot shaft causes the cam to rotate and apply a force to the junction member so as to move the junction member in the longitudinal axis; and a cam follower slideably arranged within the body, the cam follower comprising a base and a substantially rigid protrusion extending from the base, the protrusion being arranged between the dispenser driver and the junction member such that a force applied by the cam of the dispenser driver to the protrusion causes the cam follower to slideably move in the longitudinal axis of the body and apply a force to the junction member so as to release a dose of the substance from the substance source.

2. A dispenser according to claim 1, wherein the body comprises a guide for guiding the slideable motion of the cam follower base in the longitudinal axis, the guide being shaped to receive the base of the cam follower in a slideable engagement.

3. A dispenser according to claim 2, wherein the guide comprises one or more guide rails arranged and adapted to co-operate with one or more guide rails on the cam follower base such that the cam follower is slideable within the body.

4. A dispenser according to claim 1, wherein the cam follower further comprises a resiliently deformable clip disposed on a lower edge of the base for engaging with a correspondingly shaped protrusion in the body, and wherein, when the clip is engaged with the protrusion, the cam follower is retained in a longitudinal position in the body until a force is exerted on the cam follower by the cam.

5. A dispenser according to claim 1, further comprising a dose counter for indicating a number of actuations of the dispenser corresponding to a number of doses dispensed from the substance source, or a number of doses remaining in the substance source.

6. A dispenser according to claim 5, wherein the dose counter comprises:

a counter having indicia, the counter being rotatable within the body in increments about the longitudinal axis of the body;

a counter driver for driving the counter, the counter driver being coupleable to the junction member and arranged to be reciprocatably moveable within the body in the longitudinal axis with the junction member; and a drive mechanism for rotating the counter, the drive mechanism being coupled to the counter driver and configured to rotate the counter in response to longitudinal movement of the counter driver.

7. A dispenser according to claim 6, wherein the body comprises a counter driver guide configured to guide the counter driver in the body so as to prevent rotation of the counter driver in the longitudinal axis.

8. A dispenser according to claim 7, wherein the counter driver guide comprises a protrusion extending from the body, the protrusion of the counter driver guide being configured and shaped so as to co-operate with a correspondingly shaped notch in the counter driver.

9. A dispenser according to claim 6, wherein the junction member comprises one or more slots, and the counter driver comprises one or more protrusions for engaging with the junction member so as to couple the junction member and counter driver.

10. A dispenser according to claim 6, wherein the counter comprises a first ring member having first indicia and a second ring member having second indicia, each of said first and second ring members being rotatable in increments about the longitudinal axis, one or both of said first and second indicia indicating a count, and the dosage counter further comprises:

a coupling mechanism for releasably coupling said first ring member to said second ring member, to allow said first and second ring members to rotate cooperatively when coupled and to allow independent rotating of said first ring member when not coupled.

11. A dispenser according to claim 10 comprising a third ring member being coaxially arranged about said longitudinal axis.

12. A dispenser according to claim 11, wherein said third ring member comprises a limiting mechanism to limit free rotation of said second ring member relative to said third ring member about said common axis.

13. A dispenser according to claim 12, wherein said second ring member comprises a plurality of substantially equally-spaced protrusions and wherein said limiting mechanism engages with said protrusions for limiting said free rotation of said second ring member.

14. A dispenser according to claim 11, wherein said third ring member comprises one or more locating recesses disposed in an upper circumferential surface for engaging with correspondingly-shaped protrusions in a counter housing for preventing free rotation of said third ring member.

15. A dispenser according to claim 1, further comprising a substance source.

16. A dispenser according to claim 5, wherein the substance source is a pressurised metered-dose inhaler (pMDI).

17. A dispenser for dispensing a dose of a gaseous, gas borne or droplet substance from a substance source, the dispenser comprising:

a body for receiving the substance source, the body having a mouthpiece;

a junction member slideably arranged in the body for movement in a longitudinal axis of the body to release a dose of the substance from the substance source, the junction member comprising a socket for receiving a spout of the substance source; and a dose counter for indicating a number of actuations of the dispenser corresponding to a number of doses dispensed from the substance source, or a number of doses remaining in the substance source, the dose counter comprising:

a counter having indicia, the counter being rotatable within the body in increments about the longitudinal axis of the body;

a counter driver for driving the counter, the counter driver being arranged to be reciprocatably moveable within the body in the longitudinal axis in response to an actuation of the dispenser; and a drive mechanism for rotating the counter, the drive mechanism being coupled to the counter driver and configured to rotate the counter in response to longitudinal movement of the counter driver, wherein the body comprises a counter driver guide configured to guide the counter driver in the body so as to prevent rotation of the counter driver in the longitudinal axis.

18. A dispenser according to claim 17, wherein the counter driver guide comprises a protrusion extending from the body, the protrusion being configured and shaped so as to co-operate with a correspondingly shaped notch in the counter driver.

19. A dispenser according to claim 17, wherein the junction member comprises one or more slots, and the counter driver comprises one or more protrusions for engaging with the junction member so as to couple the junction member and the counter driver.

20. A dispenser for dispensing a dose of a gaseous, gas borne or droplet substance from a substance source, the dispenser comprising:

a body for receiving the substance source, the body having a mouthpiece;

a junction member slideably arranged in the body for movement in a longitudinal axis of the body to release a dose of the substance from the substance source, the junction member comprising a socket for receiving a spout of the substance source;

a dispenser driver for moving the junction member in the longitudinal axis of the body to release a dose of the substance from the substance source, the dispenser driver comprising a pivot shaft and a cam arranged on the shaft, the dispenser driver being arranged within the body such that rotation of the pivot shaft causes the cam to rotate and apply a force to the junction member so as to move the junction member in the longitudinal axis;

a cam follower slideably arranged within the body, the cam follower comprising a base and a substantially rigid protrusion extending from the base, the protrusion being arranged between the dispenser driver and the junction member such that a force applied by the cam of the dispenser driver to the protrusion causes the cam follower to slideably move in the longitudinal axis of the body and apply a force to the junction member so as to release a dose of the substance from the substance source; and a dose counter for indicating a number of actuations of the dispenser corresponding to a number of doses dispensed from the substance source, or a number of doses remaining in the substance source, the dose counter comprising:

a counter having indicia, the counter being rotatable within the body in increments about the longitudinal axis of the body;

a counter driver for driving the counter, the counter driver being arranged to be reciprocatably moveable within the body in the longitudinal axis in response to an actuation of the dispenser; and a drive mechanism for rotating the counter, the drive mechanism being coupled to the counter driver and configured to rotate the counter in response to longitudinal movement of the counter driver, wherein the body comprises a counter driver guide configured to guide the counter driver in the body so as to prevent rotation of the counter driver in the longitudinal axis.

*21. A dispenser according to claim 20, wherein the counter driver guide comprises a protrusion extending from the body, the protrusion being configured and shaped so as to co-operate with a correspondingly shaped notch in the counter driver.*

* * * * *